(12) United States Patent
Markovic et al.

(10) Patent No.: US 11,351,254 B2
(45) Date of Patent: Jun. 7, 2022

(54) HEMATOLOGIC CANCER TREATMENTS

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 550 days.

(21) Appl. No.: 15/430,411

(22) Filed: Feb. 10, 2017

(65) Prior Publication Data
US 2017/0232102 A1 Aug. 17, 2017

Related U.S. Application Data

(60) Provisional application No. 62/294,829, filed on Feb. 12, 2016.

(51) Int. Cl.
| | | |
|---|---|---|
| *A61K 39/395* | (2006.01) | |
| *A61K 9/00* | (2006.01) | |
| *A61K 9/51* | (2006.01) | |
| *C07K 16/30* | (2006.01) | |
| *A61K 9/16* | (2006.01) | |
| *A61K 31/337* | (2006.01) | |
| *C07K 16/28* | (2006.01) | |
| *A61K 39/00* | (2006.01) | |

(52) U.S. Cl.
CPC ...... *A61K 39/39558* (2013.01); *A61K 9/0019* (2013.01); *A61K 9/1658* (2013.01); *A61K 9/5169* (2013.01); *A61K 31/337* (2013.01); *A61K 39/3955* (2013.01); *C07K 16/2887* (2013.01); *C07K 16/2893* (2013.01); *C07K 16/2896* (2013.01); *C07K 16/3061* (2013.01); *A61K 2039/505* (2013.01); *C07K 2317/24* (2013.01)

(58) Field of Classification Search
CPC ............ A61K 39/39558; A61K 9/0019; A61K 9/1658; A61K 9/5169; A61K 31/337; A61K 39/3955; A61K 2039/505; A61K 47/643; A61K 47/68; A61K 47/6867; C07K 16/2887; C07K 16/2893; C07K 16/2896; C07K 16/3061; C07K 2317/24; A61P 35/02
See application file for complete search history.

(56) References Cited

U.S. PATENT DOCUMENTS

| | | | |
|---|---|---|---|
| 4,350,687 A | 9/1982 | Lipton et al. | |
| 5,026,772 A | 6/1991 | Kobayashi et al. | |
| 5,116,944 A | 5/1992 | Sivam et al. | |
| 5,216,130 A | 6/1993 | Line et al. | |
| 5,252,713 A | 10/1993 | Morgan, Jr. et al. | |
| 5,260,308 A | 11/1993 | Poduslo et al. | |
| 5,728,541 A | 3/1998 | Kornblith | |
| 5,736,137 A | 4/1998 | Anderson et al. | |
| 6,054,297 A | 4/2000 | Carter et al. | |
| 6,147,060 A | 11/2000 | Zasloff et al. | |
| 6,416,967 B2 | 7/2002 | Kornblith | |
| 6,537,579 B1 | 3/2003 | Desai et al. | |
| 6,933,129 B1 | 8/2005 | Kornblith | |
| 7,041,301 B1 | 5/2006 | Markovic | |
| 7,112,409 B2 | 9/2006 | Blumenthal et al. | |
| 7,678,552 B2 | 3/2010 | Kornblith | |
| 7,731,950 B2 | 6/2010 | Noessner et al. | |
| 7,758,891 B2 | 7/2010 | Desai et al. | |
| 7,820,788 B2 | 10/2010 | Desai et al. | |
| 7,906,121 B2 | 3/2011 | Chang et al. | |
| 7,923,536 B2 | 4/2011 | Desai et al. | |
| 8,034,375 B2 | 10/2011 | Desai et al. | |
| 8,119,129 B2 | 2/2012 | Jure-Kunkel et al. | |
| 8,138,229 B2 | 3/2012 | Desai et al. | |
| 8,268,348 B2 | 9/2012 | Desai et al. | |
| 8,314,156 B2 | 11/2012 | Desai et al. | |
| 8,344,177 B2 | 1/2013 | Neri et al. | |
| 8,735,394 B2 | 5/2014 | Desai et al. | |
| 8,853,260 B2 | 10/2014 | Desai et al. | |
| 9,101,543 B2 | 8/2015 | Desai et al. | |
| 9,387,244 B2 | 7/2016 | Markovic | |
| 9,427,477 B2 | 8/2016 | Markovic et al. | |
| 9,446,148 B2 | 9/2016 | Markovic et al. | |

(Continued)

FOREIGN PATENT DOCUMENTS

| | | |
|---|---|---|
| EP | 1 913 947 A1 | 4/2008 |
| EP | 3204413 | 8/2017 |

(Continued)

OTHER PUBLICATIONS

Package Insert, Campath® (ALEMTUZUMAB), Millennium and ILEX Partners, LP, 13 pages, available May 2001.*
"U.S. Appl. No. 15/225,542; office action dated Jul. 30, 2020".
"U.S. Appl. No. 15/286,024, office action dated Feb. 10, 2020".
"U.S. Appl. No. 15/286,024, office action dated Jul. 29, 2020".
"U.S. Appl. No. 15/359,569; office action dated Aug. 10, 2020".
"U.S. Appl. No. 15/452,669; office action dated Mar. 3, 2020".
"U.S. Appl. No. 15/456,377; office action dated Mar. 12, 2020".
"U.S. Appl. No. 15/456,377; office action dated Sep. 1, 2020".
"U.S. Appl. No. 15/456,391; office action dated Feb. 4, 2020".
"U.S. Appl. No. 15/460,699; office action dated Mar. 3, 2020".

(Continued)

*Primary Examiner* — Alana Harris Dent
(74) *Attorney, Agent, or Firm* — Baker Botts L.L.P.

(57) ABSTRACT

Disclosed herein are improved compositions and methods involved in treating hematologic cancers, i.e., cancers that begin in blood-forming tissue, such as the bone marrow, or in the cells of the immune system. The compositions comprise complexes containing albumin-containing nanoparticles (e.g., ABRAXANE® nanoparticles) and antibodies. The compositions are used to effect hematologic cancer cell death.

24 Claims, 2 Drawing Sheets

(56) References Cited

U.S. PATENT DOCUMENTS

| | | |
|---|---|---|
| 9,466,148 B2 | 10/2016 | Gay et al. |
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Markovic et al. |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,833 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Neil et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100482 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0162174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |
| 2018/0235886 A1 | 8/2018 | Markovic et al. |
| 2019/0022188 A1 | 1/2019 | Markovic |
| 2019/0038761 A1 | 2/2019 | Markovic et al. |
| 2019/0099498 A1 | 4/2019 | Markovic et al. |
| 2019/0184032 A1 | 6/2019 | Markovic et al. |
| 2019/0201546 A1 | 7/2019 | Markovic et al. |
| 2019/0202916 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |

FOREIGN PATENT DOCUMENTS

| | | |
|---|---|---|
| EP | 3533870 | 9/2019 |
| JP | S60146833 | 8/1985 |
| JP | S6178731 | 4/1986 |
| JP | H04504253 | 7/1992 |
| JP | 2001-072589 | 3/2001 |
| JP | 2012522809 | 9/2012 |
| KR | 1020090078330 | 7/2009 |
| RU | 2011133819 | 2/2013 |
| WO | WO-89/10398 A1 | 11/1989 |
| WO | 97/49390 | 12/1997 |
| WO | WO-99/00113 A1 | 1/1999 |
| WO | WO-99/51248 A1 | 10/1999 |
| WO | 2004/022097 | 3/2004 |
| WO | WO-2004/096224 A2 | 11/2004 |
| WO | 2006034455 A1 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | WO-2008/057562 A1 | 5/2008 |
| WO | WO-2008/112987 A1 | 9/2008 |
| WO | WO-2009/043159 A1 | 4/2009 |
| WO | WO-2009/055343 A2 | 4/2009 |
| WO | WO-2010/003057 A2 | 1/2010 |
| WO | WO-2010/017216 A2 | 2/2010 |
| WO | 2010/118365 | 10/2010 |
| WO | 2010/124009 | 10/2010 |
| WO | 2010136492 A1 | 12/2010 |
| WO | WO-2012/048223 A1 | 4/2012 |
| WO | WO-2012/088388 A2 | 6/2012 |
| WO | WO-2012/154861 A2 | 11/2012 |
| WO | WO-2014/009774 | 1/2014 |
| WO | 2014/037422 | 3/2014 |

(56) References Cited

FOREIGN PATENT DOCUMENTS

| WO | WO-2014/055415 A1 | 4/2014 | |
|---|---|---|---|
| WO | WO-2014105644 A1 * | 7/2014 | ........... A61K 9/5169 |
| WO | WO-2014/123612 | 8/2014 | |
| WO | 2015/048520 | 4/2015 | |
| WO | WO-2015/191969 A1 | 12/2015 | |
| WO | WO-2015/195476 A1 | 12/2015 | |
| WO | WO-2016/057554 A1 | 4/2016 | |
| WO | 2017/031368 | 2/2017 | |
| WO | 2017/062063 | 4/2017 | |
| WO | 2017/120501 | 7/2017 | |
| WO | 2017/139696 | 8/2017 | |
| WO | 2017/165439 | 9/2017 | |
| WO | 2017/165440 | 9/2017 | |
| WO | 2017/176265 | 10/2017 | |
| WO | 2016/027205 | 2/2018 | |
| WO | 2018/045233 | 3/2018 | |
| WO | 2018/045238 | 3/2018 | |
| WO | 2018/048815 | 3/2018 | |
| WO | 2018/048816 | 3/2018 | |
| WO | 2018/048958 | 3/2018 | |

OTHER PUBLICATIONS

"U.S. Appl. No. 15/461,288; office action dated Feb. 28, 2020".
"U.S. Appl. No. 15/675,596; office action dated May 28, 2020".
"U.S. Appl. No. 15/752,155; office action dated Feb. 7, 2020".
"U.S. Appl. No. 16/086,977; office action dated Sep. 3, 2020".
"U.S. Appl. No. 16/328,146; office action dated Feb. 26, 2020".
"U.S. Appl. No. 16/328,146; office action dated Jul. 28, 2020".
Barua, et al., ""Particle shape enhances specificity of antibody-display nanoparticles", PNAS 110(9):3270-3275 (2013)".
Chuang, et al., ""Recombinant human serum albumin", Drugs Today 43(8):547-561 (2007) (Abstract Only) (2 pages)".
Miele, et al., ""Albumin-bound formulation of paclitaxel (Abraxane® ABI-007) in the treatment of breast cancer", International Journal of Nanomedicine 4:99-105 (2009)".
Zhao, et al., ""Abraxane, the Nanoparticle Formulation of Paclitaxel Can Induce Drug Resistance by Ip-Regulation of P-gp", PLoS One 10(7):e0131429 (2015) (19 pages)".
Anonymous "Paclitaxel Albumin-Stabllized Nanoparticle Formulation and Bevacizumab in Treating Patients Wiih Stage IV Melanoma That Cannot Be Removed by Surgery or Gynecological Cancers", NCT02020707, ClinicalTrials.gov, Dec. 25, 2013 (13 pages).
U.S. Appl. No. 15/187,672, office action dated Sep. 11, 2019.
U.S. Appl. No. 15/225,428, office action dated Jul. 31, 2019.
U.S. Appl. No. 15/225,428, office action dated Dec. 6, 2019.
U.S. Appl. No. 15/225,542. office action dated Jan. 14, 2020.
U.S. Appl. No. 15/286,024, office action dated Aug. 1, 2019.
U.S. Appl. No. 15/359,569; office action dated Jan. 17, 2020.
U.S. Appl. No. 15/456.395; office action dated Aug. 14, 2019.
U.S. Appl. No. 15/456,399, office action dated Aug. 14, 2019.
U.S. Appl. No. 15/460,552; office; action dated Aug. 14, 2019.
U.S. Appl. No. 15/460,699; office action dated Aug. 28, 2019.
U.S. Appl. No. 15/461,288; office action dated Aug. 28, 2019.
U.S. Appl. No. 15/675,596, office action dated Dec. 3, 2010.
U.S. Appl. No. 15/752,155; office action dated Sep. 26, 2019.
Cirstoiu-Hapca et al. "Benefit of anti-HER2-coated paclitaxel-loaded immuno-nanpoarticles in the treatment of disseminated ovarian cancer: Therapeutic efficacy and biodistribution in mice", Journal of Controlled Release 144:324-331 (2010).
European Application No. 17750912.2 Extended European Search Report dated Jan. 2, 2020.
European Application No. 17771005.0, Extended European Search Report dated Oct. 17, 2019.
European Application No. 17771006.8, Extended European Search Report dated Oct. 10, 2019.
International Preliminary Report on Patentability for Application No. PCT/US2017/050134, dated Mar. 21, 2019.
Liu et al. "Freeze-Drying of Proteins", In: Walkers W., Oldenhof H. (eds) Cryopreservation and Freeze-Drying Protocols. Methods in Molecular Biology (Methods and Protocols), vol. 1257. Springer, New York, NY; published online Nov. 14. 2014.
Reynolds et al. "Phase II Trial of Nanocarlicte Albumin-Bound Paclitaxel, Carbopiatin, and Bevacizumab in First-Line Patients with Advanced Nonsquamous Non-small Cell Lung Cancer", J Thoracic Oncology 4(12):1537-1543 (2009).
Warner et al. "Alemtuzumab use in relapsed and refractory chronic lymphocytic leukemia: a history and discussion of future rational use", Ther Adv Hematol 3(6):375-389 (2012).
International Preliminary Report on Patentability corresponding to International Application No. PCT/US2017/017553 dated Aug. 23, 2018.
Abraxis Bioscience, Inc., "Abraxane Far the adjuvant treatment of node-positive breast cancer administered sequentially to standard doxorubicin-containing combination chemotherapy," Oncologic Drugs Advisory Committee Meeting (available to public Aug. 4, 2006).
Adams et al., "(P2-11-01) Safety and clinical activity of atezolizumab (anti-PDL1) in combination with nab-paclitaxel in patients with metastatic triple-negative breast cancer", 2015, XP002775314, 2015 San Antonio Breast Cancer Symposium, URL: http://sabcs.org/portals/sabcs2016/documents/sabcs-2015-abstracts.pdf?v=5.
Adams et al., "Phase lb trial of atezolizumab in combination with nab-paclitaxel in patients with metastatic triple-negative breast cancer (mTNBC)" Journal of Clinical Oncology col. 34, No. 15, May 1, 2016, 4 pages.
Anonymous, "A Phase III, Muiticenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", CiinicaiTrials.gov, Apr. 21, 2015, 1 page.
Anonymous, "Atezolizumab Plus Abraxane Promising New Treatment for Triple-Negative Breast Cancer", UNM Comprehensive Cancer Center, Jan. 7, 2016, pp. 1-2.
U.S. Appl. No. 14/116,619, office action dated Feb. 4, 2015.
U.S. Appl. No. 14/116,619, office action dated Apr. 28, 2016.
U.S. Appl. No. 14/116,619, office action mailed Sep. 10, 2015.
U.S. Appl. No. 14/432,579, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016.
U.S. Appl. No. 14/882,327, office action dated May 2, 2016.
U.S. Appl. No. 15/030,567, office action dated Sep. 7, 2016.
I U.S. Appl. No. 15/030,568, office action dated May 25, 2017.
U.S. Appl. No. 15/030,568, office action dated Jun. 18, 2018.
U.S. Appl. No. 15/030,568. office action dated Dec. 1, 2017.
U.S. Appl. No. 15/052,336, office action dated Feb. 9, 2018.
U.S. Appl. No. 15/052,623, office action dated Feb. 9, 2018.
U.S. Appl. No. 15/052,623, office action dated May 19, 2017.
U.S. Appl. No. 15/052,623, office action dated Jul. 9, 2018.
U.S. Appl. No. 15/052,623, office action dated Nov. 25, 2016.
U.S. Appl. No. 15/060.967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,433, office action dated Mar. 21, 2018.
U.S. Appl. No. 15/092,433, office action dated Oct. 11, 2017.
U.S. Appl. No. 15/187,672, office action dated May 31, 2018.
U.S. Appl. No. 15/202,115, office action dated Jan. 20, 2017.
U.S. Appl. No. 15/202,115, office action dated Sep. 26, 2016.
U.S. Appl. No. 15/225,428. office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/2.25,542, office action dated Nov. 22, 2016.
U.S. Appl. No. 15/286,006, office action dated Jan. 9, 2017.
U.S. Appl. No. 15/286.006, office action dated Jan. 18, 2018.
U.S. Appl. No. 15/286.006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,564, office action dated Jul. 10, 2018.

(56) References Cited

OTHER PUBLICATIONS

U.S. Appl. No. 15/412,510, office action dated Jul. 9, 2018.
U.S. Appl. No. 15/452,669, office action dated May 5, 2017.
U.S. Appl. No. 15/452,669, office action dated Nov. 16, 2017.
Armitage et al., "New approach to classifying non-Hodgkin's lymphomas: clinical features of the major histologic subtypes, Non-Hodgkin's Lymphoma Classification Project" J Clin Oncol 16, 2780-2795 (1998).
Baba, Oleo Science 10(1):15-18 (Jan. 2010).
Colman, "Effects of amino acid sequence changes on antibody-antigen interactions," Research in Immunology (145 (1):33-36, (1994).
Desai et al., "Enhanced antitumor activity and safety of albumin-bound nab-docetaxel versus polysorbtate 80-based docetaxel", Eur. J. Cancer, Suppl.; 18th Symposium on molecular targets and cancer therapeutics; Prague, Czech Republic, Nov. 7-10, 2006, vol. 4, No. 12, Nov. 2006 *Nov. 2006), p. 49.
Edison, "MorphoSys," 16 pages (Aug. 8, 2013).
Emens et el.; "(OT1-01-06) a phase III randomized trial of atezolizumab in combination with nab-paclitaxel as firs tline therapy for patienst with metastatic triple-negative breast cancer (mTNBC)", 2015, XP002775313, 2015 San Antonio Breast Cancer Symposium, URL: http://sabcs.org/portals/sabcs2016/documents/sabcs-2015-abstracts.pdf?v=5.
European Application No. 08743903.0 Extended European Search Report dated Jan. 24, 2911.
European Application No. 091774505.1. Extended European Search Report dated Mar. 22, 2012.
European Application No. 12781802.9, Extended European Search Report dated Dec. 18, 2014.
European Application No. 13843209.1, Extended European Search Report Application No. 13843209.1, dated Sep. 5, 2016.
European Application No. 15806443.6, Extended European Search Report dated Dec. 11, 2017.
European Application No. 15809075.3, Extended European Search Report dated Dec. 21, 2017.
Fabi et al, "Prospective study on nanoparticie albumin-bound biological observations in taxane-pretreated patients", Drug Design, 2015, 7 pages.
Flores et al., "Novel oral taxane therapies: recent Phase I results" (Apr. 1, 2013), pp. 333-341, XP055426571, UK, ISSN: 2041-6792, DOI: 10.4155/cli.13.18.
Golay et al., "Mechanism of action of therapeutic monoclonal antibodies: promises and pitfalls of in vitro and in vivo assay," Arch. Biochem. Biophys. 526(2) 146-153 (2012).
Hamilton et al, "Nab-Paclitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.
Hara, "What is anti-HER2 antibody tubulin polymerization inhibitor complex T-DM1?," Pharm. Monthly 56(5):734-739 (May 2014).
Harlow et al., Antibodies: A Laboratory Manual, Cold Spring Harbor Laboratory, New York. 1988 (9 pages).
Hassan et al: "Comparison of Different Crosslinking Methods for Preparation of Docetaxel-loaded Albumin Nanoperticies.", Iranian Journal of Pharmaceutical Research, vol. 14, No. 2, Apr. 2015 (Apr. 2015), pp. 385-394.
Hegde et al, "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.
Hood et aI., lmmunology, 1984, Benjamin, N.Y., 2nd edition.
Inman, "Atezolizumab/Nab-Paclitaxel Combo Shows High Response Rates in TNBC" OneLive, Dec. 10, 2015.
Patentability for Application No. PCT/US2015/054295 dated Oct. 13, 2016.
International Prelitninary Report on Patentability for Application PCT/US2016/026267, dated Apr. 10, 2018.
International Search Report and Written Opinion for Application No. PCT/US2015/026267, dated Jul. 12, 2016.
International Search Report and Written Opinion for Application No. PCT/US2016/026270, dated Oct. 12, 2017.
international Search Report and Written Opinion for Application No. PCT/US2016/047641, dated Oct. 31, 2016.
International Search Report and Written Opinion for Application No. PCT/US2017/012580, dated Mar. 17, 2017.
International Search Report and Written Opinion for Application No. PCT/US2017/023442, dated Jun. 16, 2017.
International Search Report and Wratten Opinion or Application No. PCT/US2017/023443, dated Jul. 11, 2017.
International Search Report and Written Opinion for Appiication No. PCT/US2017/045643, dated Oct. 25, 2017.
International Search Report and Written Opinion for Application No. PCT/US2017/049745, dated Dec. 15, 2017.
International Search Report and Written Opinion for Application No. PCT/US2017/049746, dated Nov. 27, 2017.
International Search Report and Written Opinion for Application No. PCT/US2017/050134, dated Nov. 16, 2017.
International Search Report and Written Opinion for Application No. PCT/US2017/050137, dated Nov. 27, 2017.
International Search Report and Written Opinion for Application No. PCT/US2017/050355 dated Jan. 30, 2018.
Jaime et al., "Paciltaxel antibody conjugates and trehalose for preserving the immunological activity after freeze-drying," Curr Med Chem, 2004, 11(4):439-46 Abstract Only.
Jain et al., "Normalizing tumor vasculature with anti-angiogenic therapy: a new paradigm for combination therapy," Nat. Med. 7(9):987-969 (2001).
Jain, "Normalization of uraor vasculature: an emerging concept in antiangiogenic therapy," Science 307(5706):58-62 (2005).
Jin et al., "Paclitaxel-loaded nanoparticies decorated with anti-CD133 antibody: a targeted therapy for liver cancer stem cells," J. Nanopart. Res. 2014, 16:2157 (2014).
Jin et al: "Docetaxel-loaded PEG-albumin nancparticles with improved antitumor efficiency against non-small cell lung cancer", Oncology Reports vol. 36, No. 2, Aug. 8, 2016 (Aug. 8, 2016), pp. 871-876, XP055425487, ISSN: 1021-335X, DOI: 10.3892/or.2016.4863.
Kelly et al. "Shape-Specific, Monodisperse Nano-Molding of Protein Particles," J. Am. Chem. Soc. 130:5438-5439 (2008).
Lee et al., "The co-delivery of paclitaxel and Herceptin using cationic micellar naneoarticies", Biomaterials vol. 30, No. 5, Feb. 1, 2009, pp. 919-927.
Liang et al., "IFN-alpha regulates NK cell cytotoxicity through STAT1 pathway," Cytokine, Aug. 13, 2003 (Aug. 13, 2003), vol. 23, pp. 190-199.
Makridis, et al., "MHC class I and II antigen expression and interferon ? treatment of human midgut carcinold tumors," World Journal of Surgery, Aug. 1, 1993 (Aug. 1, 1993), vol. 16, Iss. 4, pp. 481-486.
Meadows et al. "Anti-VEGF Therapies in the Clinic," Cold Spring Harbor Perspectives in Medicine, Oct. 1, 2012 (Oct. 1, 2012), vol. 2, pp. 1-27.
Mustacchi et al. "The role of taxanes in triple-negative breast cancer :liturature review", Drug Design, Development and Therapy, vol. 9, Aug. 5, 2015, 16 pages.
Nahleh at al, "Swag S0800 (NCI CDR0000636131): addition of bevacizumba to necadjuvent nab-paclitaxel with dose-dense doxorubicin and cyclophosphamide improves pathologic complete response (pCR) rates in inflammatory or locally advanced breast cancer", Breast Cancer Research and Treatment, vol. 158, No. 3 Jul. 8, 2016, 12 pages.
Nevela et al, "Abstract B77: Targeted nano-immune conjugates to melanoma: Preclinical testing of bevacizumab targeted nab-pacitaxel", Cancer Immunology Research, vol. 3, Oct. 1, 2015, 3 pages.
Nevala et al, "Antibody-targeted paclitaxel loaded nanoparticles for the treatment of CD20 B-cell lymphoma", Scientific Reports, vol, 7, Apr. 5, 2017, 9 pages.
Nevela et al, "Antibody-Targeted Chemotherapy for the Treatment of Melanoma", Cancer Research, vol. 76, No. 13, Jul. 1, 2016, pp. 3954-3964.
Nevala et al, "Targeted nano-immune conjugates to melanoma: Preclinical testing of bevacizumab targeted nab-paclitaxel", Pro-

(56) References Cited

OTHER PUBLICATIONS ceedings of the AACR Special Conference: Tumor Immunology and Immunotherapy: A New Chapter, Dec. 1. 2014, 2 pages.
Nishida et al, English Translation of "Clinical Trials of New Drugs Cytotoxic Effect against Multiple Myeloma with High Expression of a CD38 Antigen and a Human CD38 Monoclonal Antibocy Daratumumab:CD38 Antigen", history of Medicine, Sep. 29, 2012, vol. 242, No. 13, pp. 1176-1181.
Ortaldo et al., "Effects of several species of human leukocyte interferon on cytotoxic activity o fNK cells and monocytes" International Journal of Cancer, Mar. 15, 1983 (Mar. 15, 1983) vol. 31, No. 3, pp. 285-289.
Ouichi, "Antibody delivery—from basics to clinical test—Clinical development of antibody-drug conjugate," Drug. Deliv. Sys. 28(5):424-429 (2013).
Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1109.
Petrelli et al., "Targeted Delivery for Breast Cancer Therapy: the History of Nanoparticle-Albumin-Bound Paclitaxel," Expert Opinion on Pharmacotherapy, Jun. 1, 2010 (Jun. 1, 2010), vol. 11, pp. 1413-1432.
Qu Na et al: "Cabazitaxel-loaded human serum albumin nanoparticies as a therapeutic aeent against prostate cancer", International Journal of Nanomedicine, vol. 11, Jul. 26, 2016 (Jul. 26, 2016), pp. 3451-3459.
Rudikoff et al., "Single amino acid substitution altering antigen-binding specificity," Proc Natl Acad Sci USA 1982 vol. 79 pp. 1979-1983.
Samaranayake et al., "Modified taxols. 5.1 Reaction of taxol with electrophilic reagents and preparation of a rearranged taxol derivative with tubulin assembly activity", J. Org. Chem., vol. 56, 1991, pp. 5114-5119.
Soda et al "Latest topics of new medicine Albumin-bound paclitaxel," Mol. Respiratory Dis. 17(1): 109-103 (Mar. 1, 2013).
Stancovski et al., "Mechanistic aspects of the opposing effects of monoclonal antivodies to the ERBB2 receptor on tumor growth," Proc Natl Acad Sci USA, 88: 8691-8695, (1991).
Terui, English Translation of Molecular-Targeted Therapy for Cancer: Progresses and Challenges "Daratumumab. Antibody Drug against Myeloma", Pharma Med., Nov. 10, 2013, vol. 31, No. 11, p. 27-30.
Vishnu et al., "Safety and Efficacy of nab-Pacitaxel in the Treatment of Patients with Breast cancer," Breast Cancer: Basic and Clinical Research. 2011, vol. 5, pp. 53-65.
Volk et al., "Nab-paclitaxel efficacy in rhw orthotopic model of human breast cancer is significantly enhanced by concurrent antivascular endothelial growth factor A therapy," Neoplasia 10(6):613-623 (2008).
Volk-Draper et al, "Novel Model for Basaloid Triple-negative Breast Cancer: Behavior In Vivo and Responses to Therapy", vol. 14, No. 10, Oct. 1, 2012, 18 pages.
Yu et al., "Interaction between bevacizuniab and murine VEGF-A: a reassessment," Invest. Ophthalmol. Visual Sci. 49(2): 522-527, Feb. 2008.
Yuan et al., "Time-dependent vascular regression and permeability changes in established human tumor xenografts induced by an anti-vascular endothelial growth factor/vascular permeability factor antibody," Proc. Natl. Acad. Sci. USA 93(25):14765-14770 (1996).
Anonymous, "Phase I/II Study of Abraxane in Recurrent and Refractory Lymphoma", NCT01555853, ClinicalTtials.gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/225,542; office action dated Jul. 13, 2019.
U.S. Appl. No. 15/412,581, office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533: office action dated Mar. 8, 2019.
U.S. Appl. No. 15/452,669; office action dated Jun. 24, 2019.
U.S. Appl. No. 15/456,377; office action dated Mar. 19, 2019.
U.S. Appl. No. 15/456,377; office action dated Jul. 5, 2019.
U.S. Appl. No. 15/456,382; office action dated Mar. 18, 2019.
U.S. Appl. No. 15/456,382; office action dated Jul. 8, 2019.
U.S. Appl. No. 15/456,391; office action dated Mar. 15, 2019.
U.S. Appl. No. 15/456,391; office action dated Jul. 24, 2019.
U.S. Appl. No. 15/456,395; office action dated Mar. 28, 2019.
U.S. Appl. No. 15/456,399; office action dated Mar. 28, 2019.
U.S. Appl. No. 15/460,552; office action dated Apr. 1, 2019.
U.S. Appl. No. 15/460,699; office action dated Mar. 28, 2019.
U.S. Appl. No. 15/461,288: office action dated Apr. 1, 2019.
Bedu-Addo "Understanding Lyophilization Formulation Development", Pharmaceutical Technology Lyophilization, pp. 10-18 (2004).
Beers et al. "CD20 as a Target for Therapeutic Type I and II Monoclonal Antibodies", Seminars in Hematology 47 (2):107-114 (2010).
Belldegrun et al. "Human Renal Carcinoma Line Transfected with Interleukin-2 and/or Interferon alpha Gene(s) Implications for Live Cancer Vaccines", J National Cancer Institute 85(3)207-216 (1993).
Buechner "Intralesional interferon alfa-2b in the treatment of basal cell carcinoma", J Am Acad Dermatol 24:731-734 (1991).
Cheng et al. Molecularly targeted drugs for metastatic colorectal cancer. Drug Des Devel Ther. Nov. 1, 2013; 7: 1315-22 (Year: 2013).
Coiffier "The Rote of Rituximab in Lymphomas", Rev. Bras. Hematol. Hemoter., 2002. vol. 24, No. 3, ISSN: 1516-8484 (6 pages).
Doveil et al. "Adjuvant Therapy of Stage IIIb Melanoma with interferon Alfa-2b:Clinical and Immunological Relevance", Dermatology 191:234-239 (1935).
Edwards et al. The Remarkable Flexibility of the Human Antibody Repertoire; Isolation of Over One Thousand Different Antibodies to a Single Protein, BLyS, J. Mol. Biol 334:103-118 (2003).
European Application No. 16837869.3, Extended European Search Report dated Apr. 4, 2019.
European Application No. 17736453.6, Extended European Search Report dated Jul. 8, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report an Patentability for Application No. PCT/US2017/050137 dated Mar. 21, 2019.
Iqbal et al. Anti-Cancer Actions of Denosumab. Curr Osteoporas Rep. Dec. 2011;9(4): 173-6. (Year: 2011).
Khallouf et al. "5-Fluorouracil and Interferon-alpha Immunochemotherapy Enhances Immunogenicity of Murine Pancreatic Cancer Through Upregulation of NKG2D Ligands and MHC Class 1", Immunother 35(3):245-253 (2012).
Korthals et al. "Monocyte derived dendritic cells generated by IFN-alpha acquire mature dendritic and natural killer ceil properties as shown by gene expression analysis", J Translated Medicine 5:46 (2007) (11 pages).
Matthay et al. Promising therapeutic targets in neuroblastoma. Clin Cancer Res. May 15, 2012;18(10)2740-53. (Year 2012).
Reck et al. "Ipilimumab in combination with paclitaxel and carboplatin as first-line therapy in extensive-disease-small-cell lung cancer results from a randomized, double-blind, multicenter phase 2 trial", Ann Oncol. 24(1):75-83 (2013).
Robak, T. Emerging monoclonal antibodies and related agents for the treatment of chronic lymphocytic leukemia, Future Oneal. Jan. 2013;9(1):69-91. Abstract Only. (Year: 2013).
Verma et al. "Effect of surface properties on nanoparticle-cell interactions", Small. 6(1 ): 12-21. (2010).
U.S. Appl. No. 15/331,754; office action dated Feb. 22, 2019.
U.S. Appl. No. 15/359,569, office acton dated Jul. 26, 2019.
"A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: <URL: https://clinicaltrials.gov/archive/NCT00434252/200703 12>, dated Mar. 12, 2007, 3 pages.

(56) References Cited

OTHER PUBLICATIONS

"Concurrent Infusions", J Oncol Pract., 4(4): 171, Jul. 2008.
AACR Presentation, "Targeted nano-immune conjugates to melanoma: Pre-clinical testing of bevacizumab targeted nab-paclitaxel," Mayo Clinic, 2014.
ABRAXANE® for Injectable Suspension (paclitaxel protein-bound particles for injectable suspension) (albumin-bound), [drug label], 22 pages, Sep. 2009.
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(18S):8510 (Abstract).
Allen, Tm, "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II, multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patients with unresectable stage IV melanoma", U.S. National Institutes of Health, 2007, 4 pages.
Arakawa et al., "Protein-Solvent Interactions in Pharmaceutical Formulations", Pharm. Res., Mar. 1991, vol. 8, Issue 3, pp. 285-291.
Asadullah et al., "Interleukin-10 therapy-review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:S11-14.
Atkins, Michael, "Interleukin-2: clinical applications", Semin Oncol., 2002, 29(3 Suppl 7):12-27.
Avastin® Bevacizumab, Roche, [drug label], 24 pages, Sep. 2008.
Bairagi et al., Albumin: A Versatile Drug Carrier, Austin Therapeutics, (Nov. 17, 2015) vol. 2, No. 2, p. 1021 (pp. 1-6), especially abstract, p. 2, Table 2, p. 2 col. 2 para. 2.
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer, K., et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Boasberg et al., Nab-paclitaxel and bevacizumab as first-line therapy in patients with unresectable stage III and IV melanoma, J Clin Oncol., 27:15s, 2009 (suppl; abstr 9061), 2009 ASCO Annual Meeting, Retrieved from the Internet: <URL: http://meetinglibrary.asco.org/print/584876>, 2 pages, 2009.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Celis, "Overlapping human leukocyte antigen class I/II binding peptide vaccine for the treatment of patients with stage IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine, Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Davis, "Affinity separation of antibody-toxin conjugate from albumin-stabilized formulation", Am Biotechnol Lab., 12(4):60-64, Mar. 1994.
Degrasse, J.A., "A Single-Stranded DNA Aptamer That Selectively Binds to *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daratumumab, a novel therapeutic human CD38 monoclonal antibody, induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., Apr. 1, 2008, 31(2):173-181.
Elbayoumi et al., "Tumor-Targeted Nanomedicines: Enhanced Antitumor Efficacy In vivo of Doxorubicin-Loaded, Long-Circulating Liposomes Modified with Cancer-Specific Monoclonal Antibody", Clin Cancer Res., 2009, 15(6):1973-1980.
Ellyard et al., "Th2-mediated anti-tumour immunity: friend or foe?", Tissue Antigens, 2007, 70(1):1-11.
Elsadek et al., "Impact of albumin on drug delivery—New applications on the horizon", J of Controlled Release, 2011, 1-25.
Ferrara et al., "The biology of VEGF and its receptors", Nat. Med., 2003, 9:669-676.
Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).
Folkman, J., "Angiogenesis in cancer, vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.

(56) References Cited

OTHER PUBLICATIONS

Gabrilovich et al., "Production of vascular endothelial growth factor by human tumors inhibits the functional maturation of dendritic cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Graells et al., "Overproduction of VEGF16s concomitantly expressed with its receptors promotes growth and survival of melanoma cells through MAPK and PI3K signaling", J. Invest. Dermatol., 2004, 123:1151-1161.
Gupta, I., et al., "Ofatumumab, the first human anti-CD20 monoclonal antibody for the treatment of B cell hematologic malignancies," Ann. N.Y. Acad. Sci., 1263, pp. 43-56 (Jul. 25, 2012).
Haley et al., "Nanoparticles for drug delivery in cancer treatment", Urol. Oncol.: Seminars and Original Invest., 2008, 26:57-64.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.
Hersh et al., "A randomized, controlled phase III trial of nab-Paclitaxel versus dacarbazine in chemotherapy-naïve patients with metastatic melanoma", Ann Oncol, 2015, epub Sep. 26, 2015.
Hersh et al., "Open-label, multicenter, phase II trial of ABI-007 in previously treated and previously untreated patients with metastatic malignant melanoma", J. Clin. Oncol., 2005, 23(16S):7558 (Abstract).
Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites: Recovery of specific activity in an antidigoxin single-chain Fv analogue produced in *Escherichia coli*", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
International Preliminary Report on Patentability for Application No. PCT/US2012/037137 dated Nov. 12, 2013, 5 pages.
International Preliminary Report on Patentability for Application No. PCT/US2008/057025, dated Sep. 15, 2009, 6 pages.
International Preliminary Report on Patentability for Application No. PCT/US2009/049511, dated Jan. 5, 2011, 6 pages.
International Preliminary Reporton Patentability for Application No. PCT/US2013/062638, dated Apr. 16, 2015, 11 pages.
International Preliminary Report on Patentability, PCT/US2015/035505, Mayo Foundation for Medical Education and Research, 10 pages (dated Dec. 22, 2016).
International Preliminary Report on Patentability, PCT/US2015/035515, Mayo Foundation for Medical Education and Research, 18 pages (dated Dec. 29, 2016).
International Search Report and Written Opinion for Application No. PCT/US15/35505 dated Nov. 24, 2015. 17 pages.
International Search Report and Written Opinion for Application No. PCT/US15/35515 dated Sep. 21, 2015. 23 pages.
International Search Report and Written Opinion for Application No. PCT/US16/47641 dated Oct. 31, 2016, 11 pages.
International Search Report and Written Opinion for Application No. PCT/US17/17553 dated Feb. 10, 2017, 13 pages.
International Search Report and Written Opinion for Application No. PCT/US2008/057025, dated Jul. 1, 2008, 11 pages.
International Search Report and Written Opinion for Application No. PCT/US2009/049511, dated Feb. 2, 2010, 8 pages.
International Search Report and Written Opinion for Application No. PCT/US2012/037137 dated Sep. 28, 2012, 5 pages.
International Search Report and Written Opinion for Application No. PCT/US2013/062638, dated Jan. 23, 2014, 19 pages.
International Search Report and Written Opinion for Application No. PCT/US2015/054295 dated Jan. 25, 2016, 15 pages.
Jain et al., "Delivering nanomedicine to solid tumors", Nature Reviews Clinical Oncology, Nov. 2010, 7, pp. 653-664.
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paclitaxel-induced apoptosis," Mol. Cancer Ther., (2003), 2:1183-1193.
Jiang et al., "Regulation of Immune Responses by T Cells", N Engl J Med., 2006, 354(11): 1166-1176.
Julien et al., "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-small cell lung carcinoma patients", Lung Cancer, 2008, 59(1):41-47.
Kikuchi et al., "Vascular endothelial growth factor and dendritic cells in human squamous cell carcinoma of the oral cavity", Anticancer Res., 2006, 26(3A):1833-1848.
Kim et al., "A Dual Target-directed Agent against lnterleukin-6 Receptor and Tumor Necrosis Factor a ameliorates experimental arthritis", Scientific Reports, 2016, pp. 1-12.
Kim et al., "Beam: A Randomized Phase II Study Evaluating the Activity of Bevacizumab in Combination with Carboplatin Plus Paclitaxel in Patients With Previously Untreated Advanced Melanoma", Journal of Clinical Oncology: official journal of the American Society of Clinical Oncology, Jan. 1, 2012, vol. 30, No. 1, pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.
Korman et al., "Tumor immunotherapy: preclinical and clinical activity of anti-CTLA4 antibodies", Curt Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.
Kottschade et al., "A Randomized Phase 2 Study of Temozolomide and Bevacizumab or nab-Paclitaxel, Carboplatin, and Bevacizumab in Patients with Unresectable Stage IV Melanoma", Cancer, 2013, vol. 119, Issue 3, pp. 586-592.
Kratz et al., "Serum proteins as drug carriers of anticancer agents: a review", Drug Deliv., 5(4):281-299, 1998.
Kratz, "Albumin as a drug carrier: design of prodrugs, drug conjugates and nanoparticles", J Control Release, 132(3):171-183, Epub May 17, 2008.

(56) References Cited

OTHER PUBLICATIONS

Krishnan et al., "Programmed death-1 receptor and interleukin-10 in liver transplant recipients at high risk for late cytomegalovirus disease", Transpl Infect Dis., 12(4):363- 70, print Aug. 2010, ePub Jan. 2010.

Kukowska-Latallo et al., Nanoparticle Targeting of Anticancer Drug Improves Therapeutic Response in Animal Model of Human Epithelial Cancer, Cancer Res, 2005, 65(12):5317-5324.

Kumar et al., Th1/Th2 cytokine imbalance in meningioma, anaplastic astrocytoma and glioblastoma multiforme patients, Oncol. Rep., 2006, 15(6):1513-1516.

Lanzavecchia et al., "The use of hybrid hybridomas to target human cytotoxic T lymphocytes", Eur. J. Immunol., 1987, 17, pp. 105-111.

Lau et al., Is inhibition of cancer angiogenesis and growth by paclitaxel schedule dependent?, Anti-Cancer Drugs, 2004, 15:871-875.

Lei et al., Comparing cellular uptake and cytotoxicity of targeted drug carriers in cancer cell lines with different drug resistance mechanisms, Nanomed: Nanotech, Biol, and Med., 2011, 7:324-332.

Lev et al., Dacarbazine causes transcriptional up-regulation of interleukin 8 and vascular endothelial growth factor in melanoma cells: a possible escape mechanism from chemotherapy, Mol. Cancer Ther., 2003, 2:753-763.

Lev et al., Exposure of melanoma cells to dacarbazine results in enhanced tumor growth and metastasis in vivo, J. Clin. Oncol., 2004, 22:2092-2100.

Lin, S.Y, "Salmon calcitonin: conformational changes and stabilizer effects", AIMS Biophysics, 2015, 2(4): 695-723.

Lundin et al., Phase 2 Study of Alemtuzumab (anti-CD52 Monoclonal Antibody)in Patients with Advanced Mycosis Fungoides/Sezary Syndrome, Blood. (Jun. 1, 2003) vol. 101, No. 11, pp. 4267-4272, especially p. 4267 col. 1, para. 1, p. 4267 col. 2, para 2—p. 4268 col. 1, para. 1, p. 4271 col. 1, para. 3.

Marcoval et al., Angiogenesis and malignant melanoma. Angiogenesis is related to the development of vertical (tumorigenic) growth phase, J. Cutan. Pathol., 1997, 24:212-218.

Markovic et al., A phase II study of ABT-510 (thrombospondin-1 analog) for the treatment of metastatic melanoma, Am. J. Clin. Oncol., 2007, 30(3):303-309.

Markovic et al., A reproducible method for the enumeration of functional ( cytokine producing) versus non-functional peptide-specific cytotoxic T lymphocytes in human peripheral blood, Clin. Exo. Immunol., 2006, 145:438-447.

Markovic et al., Peptide vaccination of patients with metastatic melanoma: improved clinical outcome in patients demonstrating effective immunization, Am J Clin Oncol., 2006, 29(4):352-360.

Matejtschuk, P., "Lyophilization of Proteins", Methods in Molecular Biology, Cryopreservation and Freeze-Drying Protocols, Second Edition, Edited by: J. G. Day and G. N. Stacey © Humana Press Inc., Totowa, NJ, 2007, vol. 368, pp. 59-72.

Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.

Mayo Clinic: Paclitaxel Albumin-Stabilized Nanoparticle Formulation and Bevacizumab in Treating Patients With Stage IV Melanoma That Cannot Be Removed by Surgery—Full Text View ClinicalTrials.gov, Dec. 19, 2013, pp. 1-4, Retrieved from the Internet URL:https//clinicaltrials.gov/ct2/show/NCT02020707?term=targeted+nanoparticle+therapy+for+advanced+melanoma&rank=1 [retrieved on Jan. 6, 2016].

McElroy et al., Imaging of Primary and Metastatic Pancreatic Cancer Using a Fluorophore-Conjugated Anti-CA19-9 Antibody for Surgical Navigation, World J Surg., 2008, 32: 1057-1066.

Melcher, Recommendations for influenza and pneumococcal vaccinations in people receiving chemotherapy, Clin Oncol (R Coll Radiol), 2005, 17(1): 12-15.

Merchan et al., Increased endothelial uptake of paclitaxel as a potential mechanism for its antiangiogenic effects: potentiation by Cox-2 inhibition, Int. J. Cancer, 2005, 113, pp. 490-498.

Mezzaroba et al., "New potential therapeutic approach for the treatment of B-Cell malignancies using chlorambucil/Hydroxychloroquine-Loaded Anti-CD20 Nanoparticles", Sep. 2103, PLoS ONE vol. No. 8, Issue 9 pp. 1-10, e74216.

Middleton et al., Randomized phase III study of temozolomide versus dacarbazine in the treatment of patients with advanced metastatic malignant melanoma, J. Clin. Oncol., 2000, 18, pp. 158-166.

Miller et al. "Paclitaxel plus Bevacizumab versus Paclitaxel Alone for Metastatic Breast Cancer," N Engl. J Med., (2007) vol. 357:2666-2676.

Mimura et al., Vascular endothelial growth factor inhibits the function of human mature dendritic cells mediated by VEGF receptor-2, Cancer Immunol Immunother., 2007, 56(6). pp. 761-770.

Mirtsching et al., "A Phase II Study of Weekly Nanoparticle Albumin-Bound Paclitaxel With or Without Trastuzumab in Metastatic Breast Cancer", Clinical Breast Cancer, 2011, 11(2):121-128.

Mocellin et al., Cytokines and immune response in the tumor microenvironment, J Immunother., 2001, 24(5), pp. 392-407.

Motl, S., Bevacizumab in combination chemotherapy for colorectal and other cancers, Am. J. Health-Syst. Pharm 2005, 62:1021-1032.

Ng et al., Influence of formulation vehicle on metronomic taxane chemotherapy: albumin-bound versus cremophor EL-based paclitaxel, Clin. Cancer Res., 2006, 12, pp. 4331-4338.

Ng et al., Taxane-mediated antiangiogenesis in vitro: influence of formulation vehicles and binding proteins, Cancer Res., 2004, 64, pp. 821-824.

Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.

Oku et al., Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts, Cancer Res., 1998, 58, pp. 4185-4192.

Parikh et al., The vascular endothelial growth factor family and its receptors, Hematol. Oncol. Clin. N. Am., 2004, 18, pp. 951-971.

Park et al., Anti-HER2 Immunoliposomes: Enhanced Efficacy Attributable to Targeted Delivery, Clin. Cancer Res., 2002, 8, pp. 1172-1181.

Perez et al., "Phase 2 trial of carboplatin, weekly paclitaxel, and biweekly bevacizumab in patients with unresectable stage IV melanoma," A north central cancer treatment group study, Cancer, 2009, 115(1), pp. 119-127.

Phase II: A Study of Bevacizumab With Carboplatin and Paclitaxel Chemotherapy for the First-Line Treatment of Patients With Metastatic Melanoma (BEAM) Mar. 12, 2007, [retrieved Mar. 15, 2010], Retrieved from the Internet: <URL:http://clinicaltrials.gov/archive/NCT00434252/2007 03 12>, 3 pages.

Pikal, M., Freeze-drying of proteins, Part II: Formulation selection, Biopharm, 1990, 9, pp. 26-30.

Polak et al., Mechanisms of local immunosuppression in cutaneous melanoma, Br J Cancer, 2007, 96(12), pp. 1879-1887.

Porrata et al., Early lymphocyte recovery predicts superior survival after autologous hematopoietic stem cell transplantation in multiple myeloma or non-Hodgkin lymphoma, Blood, 2001, 98(3), pp. 579-585.

Porrata et al., Timely reconstitution of immune competence affects clinical outcome following autologous stem cell transplantation, Clin Exp Med., 2004, 4(2):78-85.

Powell et al., Adoptive transfer of vaccine-induced peripheral blood mononuclear cells to patients with metastatic melanoma following lymphodepletion, J Immunol., 2006, 177(9), pp. 6527-6539.

Pries et al., Cytokines in head and neck cancer, Cytokine Growth Factor Rev., 2006, 17(3), pp. 141-146.

Ranieri et al., "Vascular endothelial growth factor (VEGF) as a target of bevacizumab in cancer: from the biology to the clinic", Curr. Med. Chem., 2006, 13, 1845-1857.

(56) References Cited

OTHER PUBLICATIONS

Rao et al., "Combination of paclitaxel and carboplatin as second-line therapy for patients with metastatic melanoma", Cancer, 2006, 106(2), 375-382.
Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen-specific CD8+T cells in patients with melanoma", J. Immunol., 2005, 175(9), pp. 6169-6176.
Roy et al., "Tumor associated release of interleukin-10 alters the prolactin receptor and down-regulates prolactin responsiveness of immature cortical thymocytes", J Neuroimmunol., 2007, 186(1-2), pp. 112-120.
Rudnicka et al., "Rituximab causes a polarization of B cells that augments its therapeutic function in NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-86.
Salven et al., "Enhanced expression of vascular endothelial growth factor in metastatic melanoma", Br. J. Cancer, 1997, 76(7), pp. 930-934.
Sandler et al., "Paclitaxel-carboplatin alone or with bevacizumab for non-small-cell lung cancer", N. Engl. J. Med., 2006, 355:2542-2550.
Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.
Schrama et al., "Antibody targeted drugs as cancer therapeutics, Nature Reviews Drug Discovery", Feb. 2006, 5, pp. 147-159.
Sester et al., "Differences in CMV-specific T-cell levels and long-term susceptibility to CMV infection after kidney, heart and lung transplantation", Am J Transplant., 5(6): 1483-1489, Jun. 2005.
Srivastava et al., "Angiogenesis in cutaneous melanoma: pathogenesis and clinical implications", Microsc. Res. Tech., 2003, 60:208-224.
Streit et al., "Angiogenesis, lymphangiogenesis, and melanoma metastasis", Oncogene, 2003, 22, pp. 3172-3179.
Taieb et al., "Chemoimmunotherapy of tumors: Cyclophosphamide synergizes with exosome based vaccines", J. Immunol., Mar. 1, 2006, 176(5):2722-2729.
Tao et al., "Inhibiting the growth of malignant melanoma by blocking the expression of vascular endothelial growth factor using an RNA interference approach", Br. J. Dermatol., 2005, 153:715-724.
Tas et al., "Circulating serum levels of angiogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 897-901.
Ugurel et al., "Increased serum concentration of angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Vence et al., "Circulating tumor antigen-specific regulatory T cells in patients with metastatic melanoma", Proc Natl Acad Sci USA, 2007, 104(52), pp. 20884-20889.

Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.
Walker et al., "Monitoring immune responses in cancer patients receiving tumor vaccines", Int Rev Immunol., 2003, 22(3-4):283-319.
Wang et al., "Biofunctionalized targeted nanoparticles for therapeutic applications", Expert Opin. Biol. Ther., 2008, 8(8): 1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-19.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial oftaxol given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.
Wu et al., "Aptamers: Active Targeting Ligands for Cancer Diagnosis and Therapy", Theranostics, 2015, 5(4):322-344.
Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.
Yuan et al., "Vascular Permeability in a Human Tumor Xenograft: Molecular Size Dependence and Cutoff Size", Cancer Research, Sep. 1, 1995, 55, pp. 3752-3756.
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.
U.S. Appl. No. 14/432,979, office action dated Jan. 7, 2019.
U.S. Appl. No. 15/052,336, office action dated Jan. 22, 2019.
U.S. Appl. No. 15/052,336, office action dated Sep. 4, 2018.
U.S. Appl. No. 15/052,623, office action dated Jan. 7, 2019.
U.S. Appl. No. 15/092,403, office action dated Oct. 4, 2018.
U.S. Appl. No. 15/092,433, office action dated Aug. 10, 2018.
U.S. Appl. No. 15/092,433; office action dated Dec. 12, 2018.
U.S. Appl. No. 15/187,672, office action dated Nov. 28, 2018.
U.S. Appl. No. 15/225,428, office action dated Aug. 14, 2018.
U.S. Appl. No. 15/331,754; office action dated Oct. 11, 2018.
U.S. Appl. No. 15/412,536, office action dated Oct. 1, 2018.
U.S. Appl. No. 15/412,554, office action dated Sep. 27, 2018.
U.S. Appl. No. 15/412,581; office action dated Nov. 13, 2018.
U.S. Appl. No. 15/412,596, office action dated Sep. 4, 2018.
U.S. Appl. No. 15/412,596, office action dated Dec. 27, 2018.
U.S. Appl. No. 15/413,257; office action dated Sep. 25, 2018.
U.S. Appl. No. 15/414,526; office action dated Nov. 16, 2018.
U.S. Appl. No. 15/414,533; office action dated Nov. 19, 2018.
U.S. Appl. No. 15/414,536; office action dated Oct. 11, 2018.
U.S. Appl. No. 15/452,669, office action dated Nov. 26, 2018.
Elst et al. "Epidermal Growth Factor Receptor Expression and Activity In Acute Myeloid Leukemia", Blood 116:3144 (2010), abstract.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442, dated Oct. 4, 2018.
International Preliminary Report on Patentability for Application No. PCT/US2017/023443, dated Oct. 4, 2018.

(56) References Cited

OTHER PUBLICATIONS

Lloyd et al. "Modelling the human immune response; performance of a 1011 human antibody repertoire against a broad panel of therapeutically relevant antigens", Protein Eng., Design & Selection 22(3):159-168 (2009).
Washington School of Medicine: "Phase I/II study of Abraxane in recurrent and refractory lymphoma NCT01555853," ClinicalTrials.gov, Mar. 16, 2012.

\* cited by examiner

HEMATOLOGIC CANCER TREATMENTS

CROSS-REFERENCE TO RELATED APPLICATION

This application claims the benefit of U.S. Provisional Application No. 62/294,829, filed Feb. 12, 2016, the disclosure of which is considered part of, and is incorporated by reference in, the disclosure of this application.

TECHNICAL FIELD

This invention relates to improved compositions and methods involved in treating hematologic cancers, i.e., cancers that begin in blood-forming tissue, such as the bone marrow, or in the cells of the immune system, e.g., leukemia (e.g., acute myelogenous (granulocytic) leukemia (AML), chronic myelogenous (granulocytic) leukemia (CML), acute lymphocytic (lymphoblastic) leukemia (ALL), chronic lymphocytic leukemia (CLL), and hairy cell leukemia), lymphomas (e.g., mature B-cell neoplasms, mature T cell neoplasms, mature natural killer cell neoplasms, immunodeficiency-associated lymphoproliferative disorders, Hodgkin lymphomas, and non-Hodgkin lymphomas), myeloma (e.g., multiple myeloma). This invention also relates to compositions and methods using complexes containing albumin-containing nanoparticles (e.g., ABRAXANE® nanoparticles) and antibodies (e.g., anti-CD20 polypeptide antibodies such as Rituximab) to treat hematologic cancers, e.g., leukemias, lymphomas and myelomas. The results presented herein demonstrate the criticality of administering an effective dose of the complexes of albumin-containing nanoparticles (e.g., ABRAXANE® nanoparticles) and antibodies to achieve regression of the cancer.

BACKGROUND

Hematologic cancers are cancers that begin in blood-forming tissue, such as the bone marrow, or in the cells of the immune system. Examples of hematologic cancer are leukemia, lymphoma, and multiple myeloma.

SUMMARY

ABRAXANE® (nanosized particles of albumin and paclitaxel commercially available from Celgene Corp.) provided a novel approach to treating cancers with paclitaxel. However notwithstanding its blood compatibility, ABRAXANE® is ineffective against hematological cancers. As such, conventional protocols and treatment regimens are still used, along with exploratory immunotherapies, in the treatment of hematologic cancers.

This invention provides improvements in the methods and materials involved in treating hematologic cancers, e.g., leukemias (e.g., AML, CML, ALL, CLL, and hairy cell leukemia), lymphomas (e.g., mature B-cell neoplasms, mature T cell neoplasms, mature natural killer cell neoplasms, immunodeficiency-associated lymphoproliferative disorders, Hodgkin lymphomas, and non-Hodgkin lymphomas), and myelomas (e.g., multiple myeloma, light chain myeloma, and non-secretory myeloma).

In one embodiment, this invention provides pharmaceutical compositions comprising complexes containing albumin-containing nanoparticles (e.g., ABRAXANE® nanoparticles) and humanized or chimeric antibodies and methods for treating a hematologic cancer using the pharmaceutical compositions. The antibodies include without limitation, e.g., anti-CD52 polypeptide antibodies and anti-CD20 polypeptide antibodies to treat leukemias, anti-CD20 polypeptide antibodies to treat lymphomas, and anti-CD38 polypeptide antibodies to treat myelomas. Such antibodies also include, e.g., Alemtuzumab, Obinutuzumab, Rituximab, Daratumumab, MOR202, or SAR650984.

Without being bound by theory, humanized monoclonal antibodies contain a hydrophobic Fc portion comprising hydrophobic amino acids. Likewise albumin contains a hydrophobic and a hydrophilic domain. It is the hydrophobic domain of albumin that solubilizes paclitaxel. The hydrophobic domain of albumin allows for surface complexation of the hydrophobic Fc portion of the humanized antibody and such hydrophobic-hydrophobic interactions are sufficiently stable to permit retention of the structural motif of the albumin-paclitaxel particles. Surprisingly the structural motif is stable to lyophilization. Accordingly, this invention is directed in part to lyophilized compositions, e.g., compositions comprising albumin-containing nanoparticles complexed with an antibody wherein said nanoparticles contain albumin and a therapeutically effective amount of paclitaxel contained therein, as well as a plurality of the antibodies complexed with the nanoparticles, wherein said nanoparticles are solids which complexes have a size less than 1 micron provided that at least a portion of the antibodies are arranged on the surface of the nanoparticles in a manner that the nanoparticle-complexes retain antibody mediated target binding specificity, wherein the composition is in a lyophilized form. The antibodies are preferably humanized antibodies directed to hematological cancer cells. The antibodies can be, e.g., a humanized anti-CD52 polypeptide antibody, a humanized anti-CD20 polypeptide antibody, or a humanized anti-CD38 polypeptide antibody.

An embodiment of this invention includes, unit dose of a composition comprising albumin-containing nanoparticles complexed with an antibody wherein said nanoparticles contain albumin and paclitaxel at a ratio of about 9:1 albumin to paclitaxel as well as a plurality of humanized antibodies complexed thereto wherein said nanoparticles are solids which complexes have a size less than 1 micron provided that at least a portion of the said antibodies are arranged on the surface of said nanoparticles in a manner that said nanoparticle-complexes retain antibody mediated target binding specificity, wherein said unit dose comprises from about 17.5 mg/m$^2$ to about 125 mg/m$^2$ of said antibody and about 75 mg/m$^2$ to about 250 mg/m$^2$ paclitaxel. The unit dose may also comprise 100 mg/m$^2$ to about 200 mg/m$^2$, or about 150 mg/m$^2$ of paclitaxel. The unit dose may also comprise about 35 mg/m$^2$ to about 100 mg/m$^2$, or about 50 to about 100 mg/m$^2$ of antibody. The antibody may be a humanized anti-CD52 polypeptide antibody, a humanized anti-CD20 polypeptide antibody or and humanized anti-CD38 polypeptide antibody The methods described herein provide for hematologic cancer cell death by contacting the cells with the compositions comprising complexes of albumin-containing nanoparticles (e.g., ABRAXANE® nanoparticles) and humanized or chimeric antibodies. The antibodies may be humanized or chimeric anti-CD52 polypeptide antibodies, anti-CD-20 polypeptide antibodies or anti-CD38 polypeptide antibodies. The hematologic cancer cell can be a leukemia cell, a lymphoma cell, or myeloma cell. The leukemia cell may be (e.g., AML cell, CML cell, ALL cell, CLL cell, and hairy cell leukemia cell), lymphoma cell can be from e.g., mature B-cell neoplasms, mature T cell neoplasms, mature natural killer cell neoplasms, immunodeficiency-associated lymphoproliferative disorders, Hodgkin lymphomas, and non- Hodgkin lymphomas, and the myeloma cell can be from, e.g., a multiple myeloma, a light chain myeloma, and a non-secretory myeloma.

The methods described herein also provide for hematologic cancer cell death in a patient by administering to the patient an effective amount of the compositions described herein comprising complexes of albumin-containing nanoparticles (e.g., ABRAXANE® nanoparticles) and humanized or chimeric antibodies. The antibodies may be humanized or chimeric anti-CD52 polypeptide antibodies, anti-CD-20 polypeptide antibodies or anti-CD38 polypeptide antibodies. The hematologic cancer cell can be a leukemia cell, a lymphoma cell, or myeloma cell.

ABRAXANE® is available from Celgene Corp. and is a nanoparticle formulation that combines paclitaxel with human albumin. Anti-CD52 polypeptide antibodies such as Alemtuzumab is available from Genzyme Corporation under trade names such as Campath. Alemtuzumab is a humanized monoclonal antibody that binds to CD52, a protein present on the surface of mature lymphocytes, but not on the stem cells from which these lymphocytes are derived. Anti-CD20 polypeptide antibodies such as Rituximab are available from Genentech Inc., Roche, and Aryogen Biopharma under trade names such as Rituxan™ MabThera™, and Zytux™. Rituximab is a chimeric monoclonal antibody against CD20 polypeptides presents on surface of lymphocyte cells (see, e.g., U.S. Pat. No. 5,736,137). Anti-CD38 polypeptide antibodies such as Daratumumab, MOR202, or SAR650984 are available from Johnson & Johnson/Genmab, Celgene Corp./Morphosys, or Sanofi/Immunogen, respectively. Daratumumab is a monoclonal antibody against CD38 polypeptides (see, e.g., de Weers et al., J Immunol., 186(3): 1840-1848 (2011)).

As described herein, combining in vitro albumin-containing nanoparticles (e.g., ABRAXANE® nanoparticles) and humanized antibodies, including e.g., anti-CD52, anti-CD20 or anti-CD38 polypeptide antibodies, e.g., Alemtuzumab, Rituximab, or SAR650984, result in the formation of macromolecular complexes, the characteristics of which (e.g., size, antibody content, or chemotherapeutic drug content) can be customized depending on need. Such macromolecular complexes retain antibody mediated target binding specificity and retain and possibly enhance chemotherapeutic tumor cell cytotoxicity, and can exhibit no additional toxicity beyond that of ABRAXANE® nanoparticles alone. As also described herein, contacting albumin-containing nanoparticles (e.g., ABRAXANE®) with a humanized or chimeric anti-CD52, anti-CD20, or anti-CD38 polypeptide antibody (e.g., Alemtuzumab, Rituximab, or SAR650984) prior to administration to a human (e.g., a human hematologic cancer patient) result in complex formation. These complexes, when administered, have an ability to treat the hematologic cancer as compared to a treatment regimen that includes administering albumin-paclitaxel nanoparticles, (e.g., ABRAXANE®) alone. Moreover, these complexes are significantly superior to treatment with ABRAXANE® and the antibody separately in a manner that does not form ABRAXANE®/antibody complexes. Moreover, the macromolecular complexes of the humanized antibody and paclitaxel albumin-containing nanoparticles are more stable as compared to the paclitaxel albumin containing nanoparticles and, therefore, provide enhanced efficacy and reduced toxicity.

This invention is predicated, in part, on the discovery that that the macromolecular complexes deliver an effective dose of paclitaxel to kill hematologic cancer cells even though the complexes comprise a dose of the antibody that is substantially lower than the standard dose of antibody heretofore used either by itself or with paclitaxel (e.g., in ABRAXANE®). For example, a unit dose of a composition of this invention comprises from about 75 mg/m$^2$ to about 250 mg/m$^2$ of paclitaxel and from about 17.5 mg/m$^2$ to about 125 mg/m$^2$, about 35 mg/m$^2$ to about 100 mg/m$^2$, and about 50 to about 100 mg/m$^2$ of an antibody described herein.

Without being limited to any theory, the use of such a small amount of antibody is possible as it imparts both in vivo stability to the compositions once administered and provides directional (steering) capacity of the nanoparticles to direct them to the cancer cells.

The methods and materials provided herein can be used to increase the progression-free survival rate in hematologic cancer patients. Increasing progression-free survival is a benefit in its own right and can lead to hematologic cancer patients to live longer.

In general, one aspect of this document features a method for treating a mammal having a hematologic cancer, e.g. a leukemia, lymphoma, or myeloma. The method comprises, or consisting essentially of, administering to the mammal a composition comprising nanoparticles containing albumin and paclitaxel complexed with an appropriate humanized or chimeric antibody, e.g., an anti-CD52 or anti-CD20 polypeptide antibody for leukemia, an anti-CD20 polypeptide antibody for lymphoma or an anti-CD38 polypeptide antibody for myeloma, under conditions wherein the length of progression-free survival is increased. The mammal can be a human. The hematologic cancer may be a leukemia (e.g., chronic lymphocytic leukemia (CLL), cutaneous T-cell lymphoma (CTCL) and T-cell lymphoma), lymphomas (e.g., mature B-cell neoplasms, mature T cell neoplasms, mature natural killer cell neoplasms, immunodeficiency-associated lymphoproliferative disorders, Hodgkin lymphomas, and non-Hodgkin lymphomas), and myelomas (e.g., multiple myeloma, light chain myeloma, and non-secretory myeloma). The composition can comprise Alemtuzumab, Rituximab, or Daratumumab complexed with the nanoparticles. The composition can also comprise an alkylating agent complexed with the nanoparticles. The alkylating agent can be a platinum compound. The platinum compound can be carboplatin. The antibody can be a humanized antibody. The antibody can be a chimeric antibody. The composition can be administered by injection.

The progression-free survival rate for patients can be increased by 15 percent or more. Preferably, the progression-free survival can be increased by 25 percent. More preferably, the progression-free survival can be increased by 50 percent. Even more preferably, the progression-free survival can be increased by 75 percent. Most preferably, the progression-free survival can be increased by at least 100 percent.

In another aspect, this document features a method for treating a mammal having a hematologic cancer, e.g., a leukemia, lymphoma or myeloma. The method comprises, or consists essentially of, administering, to the mammal, a composition comprising albumin-containing nanoparticle/antibody complexes, wherein the average diameter of the complexes is between 0.1 and 0.9 µm, and wherein the antibody is a humanized or chimeric antibody that binds to a polypeptide on the hematologic cancer cell. The polypeptide may be, e.g., a CD52 polypeptide, a CD20 polypeptide or a CD38 polypeptide. The antibody may be a humanized or chimeric antibody, e.g., a humanized or chimeric anti-CD52 polypeptide antibody, a humanized or chimeric anti-CD20 polypeptide antibody, a humanized or chimeric anti-CD38 polypeptide antibody. The mammal can be a human.

The hematologic cancer may be a leukemia (e.g., AML, CML, ALL, CLL, and hairy cell leukemia), a lymphoma (e.g., mature B-cell neoplasm, a mature T cell neoplasm, a Hodgkin lymphoma), a myeloma (e.g., multiple myeloma). The albumin-containing nanoparticle/antibody complexes can be ABRAXANE®/Rituximab complexes. The albumin-containing nanoparticle/antibody complexes can be ABRAXANE®/Alemtuzumab complexes. The albumin-containing nanoparticle/antibody complexes can be ABRAXANE®/SAR650984 complexes. The composition or the albumin-containing nanoparticle/antibody complexes can comprise an alkylating agent. The alkylating agent can be a platinum compound. The platinum compound can be carboplatin. The composition can comprise an anti-inflammatory agent. The composition can be administered by injection.

As above, the administration of these composition can be effective to increase progression-free survival of the treated mammal. The administration of the composition can be under conditions wherein the median time to progression for a population of mammals with the hematologic cancer is at least 150 days. The administration of the composition can be under conditions wherein the median time to progression for a population of mammals with the hematologic cancer is at least 165 days. The administration of the composition can be under conditions wherein the median time to progression for a population of mammals with the hematologic cancer is at least 170 days.

The average diameter of the complexes can be from 0.1 µm to 0.3 µm. The average diameter of the complexes can be from 0.15 µm to 0.3 µm. The average diameter of the complexes can be from 0.2 µm to 0.5 µm. The average diameter of the complexes can be from 0.3 µm to 0.5 µm. The average diameter of the complexes can be from 0.2 µm to 0.8 µm. The average diameter of the complexes can be from 0.2 µm to 0.7 µm.

In another aspect, this document features a method for treating a mammal having hematologic cancer. The method comprises, or consists essentially of, administering, to the mammal, a composition comprising albumin-containing nanoparticle/antibody complexes, wherein the average diameter of the complexes of the composition is between 0.1 and 0.9 µm, and wherein the antibodies are anti-CD52 antibodies, anti-CD20 antibodies, or anti-CD38 antibodies. The mammal can be a human. The hematologic cancer may be a leukemia, a lymphoma or a myeloma. The leukemia may be, e.g., AML, CML, ALL, CLL, and hairy cell leukemia. The lymphoma can be a mature B-cell neoplasm. The lymphoma can be a mature T cell neoplasm. The lymphoma can be a Hodgkin lymphoma. The myeloma may be a multiple myeloma. The albumin-containing nanoparticle/antibody complexes can be ABRAXANE®/Rituximab complexes. The albumin-containing nanoparticle/antibody complexes can be ABRAXANE®/Alemtuzumab complexes. The albumin-containing nanoparticle/antibody complexes can be ABRAXANE®/SAR650984 complexes.

The composition or the albumin-containing nanoparticle/antibody complexes can comprise an alkylating agent. The alkylating agent can be a platinum compound. The platinum compound can be carboplatin. The composition can comprise an anti-inflammatory agent. The antibody is a humanized or chimeric antibody. The antibody may be a humanized or chimeric anti-CD52 polypeptide antibodies. The antibody may be a humanized or chimeric anti-CD20 polypeptide antibodies. The antibody may be a humanized or chimeric anti-CD38 polypeptide antibodies. The composition can be administered by injection. Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
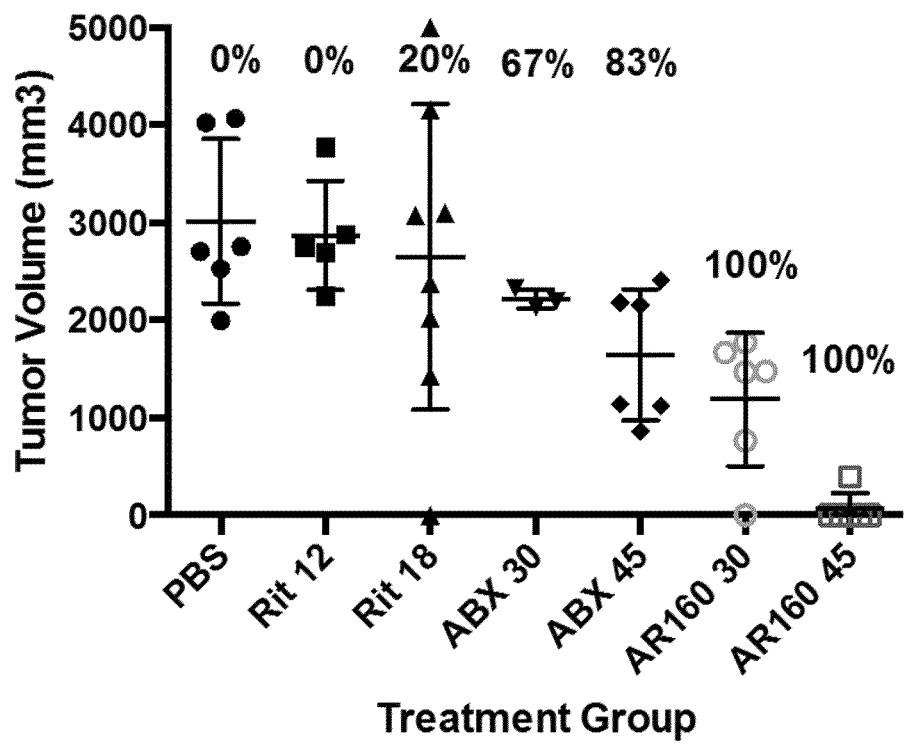
FIG. 1 presents a graph plotting percent change at ten days in tumor size from baseline of lymphoma (Daudi cell line) tumor bearing nude mice treated with PBS, Rituxan (RIT12; 12 mg/kg) only, Rituxan (RIT18; 18 mg/kg) ABRAXANE® (ABX30, 30 mg/kg) only, ABRAXANE® (ABX45, 45 mg/kg) only, AR160 30 and AR160 45 complexes.

This invention provides methods and materials involved in treating lymphomas (e.g., mature B-cell neoplasms, mature T cell neoplasms, mature natural killer cell neoplasms, immunodeficiency-associated lymphoproliferative disorders, Hodgkin lymphomas, and non-Hodgkin lymphomas). For example, this invention provides methods and materials for using complexes containing albumin-containing nanoparticles (e.g., ABRAXANE® nanoparticles) and antibodies (e.g., anti-CD20 polypeptide antibodies such as Rituximab) to treat hematologic cancers, e.g., leukemias, lymphomas, and myelomas.

The methods and materials provided herein can be used to treat any type of hematologic cancer. For example, the methods and materials provided herein can be used to treat leukemias (e.g., AML, CML, ALL, CLL, and hairy cell leukemia), Lymphomas, (e.g., mature B-cell neoplasms, mature T cell neoplasms, mature natural killer cell neoplasms, immunodeficiency-associated lymphoproliferative disorders, Hodgkin lymphomas, and non-Hodgkin lymphomas), and myelomas (e.g., multiple myeloma, light chain myeloma, and non-secretory myeloma). In some cases, the methods and materials provided herein can be used to treat hematologic cancer in any type of mammal including, without limitation, mice, rats, dogs, cats, horses, cows, pigs, monkeys, and humans.

In some cases, complexes containing albumin-containing nanoparticles (e.g., ABRAXANE® nanoparticles) and antibodies (e.g., anti-CD52 polypeptide antibodies such as Alemtuzumab, anti-CD20 polypeptide antibodies such as Rituximab and anti-CD38 polypeptide antibodies such as SAR650984). can be designed to have an average diameter that is greater than 1 μm. For example, appropriate concentrations of albumin-containing nanoparticles and antibodies can be used such that complexes having an average diameter that is greater than 1 μm are formed. Preparations of albumin-containing nanoparticle/antibody complexes provided herein having an average diameter that is greater than 1 μm should be administered into a tumor (e.g., intratumorally) or in a region of a tumor located within a mammal's body.

In some cases, complexes containing albumin-containing nanoparticles (e.g., ABRAXANE® nanoparticles) and antibodies (e.g., anti-CD52 polypeptide antibodies such as Alemtuzumab, anti-CD20 polypeptide antibodies such as Rituximab and anti-CD38 polypeptide antibodies such as SAR650984) can be designed to have an average diameter that is less than 1 μm. For example, appropriate concentrations of albumin-containing nanoparticles and antibodies (e.g., Alemtuzumab, Rituximab and SAR650984) can be used such that complexes having an average diameter that is less than 1 μm are formed. In some cases, the preparations of albumin-containing nanoparticle/antibody complexes provided herein can have an average diameter that is between 0.1 μm and 1 μm (e.g., between 0.1 μm and 0.95 μm, between 0.1 μm and 0.9 μm, between 0.1 μm and 0.8 μm, between 0.1 μm and 0.7 μm, between 0.1 μm and 0.6 μm, between 0.1 μm and 0.5 μm, between 0.1 μm and 0.4 μm, between 0.1 μm and 0.3 μm, between 0.1 μm and 0.2 μm, between 0.2 μm and 1 μm, between 0.3 μm and 1 μm, between 0.4 μm and 1 μm, between 0.5 μm and 1 μm, between 0.2 μm and 0.6 μm, between 0.3 μm and 0.6 μm, between 0.2 μm and 0.5 μm, or between 0.3 μm and 0.5 μm).

Preparations of albumin-containing nanoparticle/antibody complexes provided herein having an average diameter that is between 0.1 μm and 0.9 μm can be administered systemically (e.g., intravenously) to treat a hematologic cancer located within a mammal's body.

In general, albumin-containing nanoparticles such as ABRAXANE® can be contacted with an antibody such as an anti-CD20 polypeptide antibody (e.g., Alemtuzumab, Rituximab and SAR650984) prior to administration to a human to form an albumin-containing nanoparticle/antibody complex (e.g., an ABRAXANE®/anti-CD52 polypeptide antibody complex, an ABRAXANE®/anti-CD20 polypeptide antibody complex, or an ABRAXANE®/anti-CD38 polypeptide antibody complex). Any appropriate albumin-containing nanoparticle preparation and any appropriate antibody can be used as described herein. For example, ABRAXANE® nanoparticles can be used as described herein. Examples of antibodies that can be used to form albumin-containing nanoparticle/antibody complexes as described herein include, without limitation, Alemtuzumab, SAR650984, Rituximab (e.g., Rituxan™, MabThera™, or Zytux™). For example, an appropriate dose of ABRAXANE® and an appropriate dose of Alemtuzumab, SAR650984, or Rituximab can be mixed together in the same container. This mixture can be incubated at an appropriate temperature (e.g., room temperature, between 15° C. and 30° C., between 15° C. and 25° C., between 20° C. and 30° C., or between 20° C. and 25° C.) for a period of time (e.g., about 30 minutes, or between about 5 minutes and about 60 minutes, between about 5 minutes and about 45 minutes, between about 15 minutes and about 60 minutes, between about 15 minutes and about 45 minutes, between about 20 minutes and about 400 minutes, or between about 25 minutes and about 35 minutes) before being administered to a hematologic cancer patient (e.g., a lymphoma patient).

In some cases, albumin-containing nanoparticles such as ABRAXANE® can be contacted with an antibody such as an anti-CD52 polypeptide antibody (e.g., Alemtuzumab), anti-CD20 polypeptide antibody (e.g., Rituximab), or anti-CD38 polypeptide antibody (e.g., SAR650984) to form albumin-containing nanoparticle/antibody complexes (e.g., ABRAXANE®/antibody complexes) that are stored prior to being administered to a hematologic cancer patient (e.g., a lymphoma patient). For example, a composition containing albumin-containing nanoparticle/antibody complexes can be formed as described herein and stored for a period of time (e.g., days or weeks) prior to being administered to a cancer patient. Storage can take the form of a lyophilized composition or an aqueous composition.

Any appropriate method can be used to obtain albumin-containing nanoparticles such as ABRAXANE® and an antibody such as an anti-CD52 polypeptide antibody, an anti-CD20 polypeptide antibody or an anti-CD38 polypeptide antibody. For example, ABRAXANE® can be obtained from Celgene Corp. or as described elsewhere (U.S. Pat. No. 6,537,579). Rituximab can be obtained from Genentech Corp. or Roche Corp. or as described elsewhere (U.S. Pat. No. 5,736,137). Alemtuzumab can be obtained from Genzyme Corporation. SAR650984 can be obtained from Sanofi-Aventis.

In some cases, the combination of an albumin-containing nanoparticle such as ABRAXANE® and an antibody such as an anti-CD52 polypeptide antibody, an anti-CD20 polypeptide antibody or an anti-CD38 polypeptide antibody can include one or more other agents such as an alkylating agent (e.g., a platinum compound). Examples of platinum compounds that can be used as an alkylating agent include, without limitation, carboplatin (PARAPLATIN®), cisplatin (PLATINOL®), oxaliplatin (ELOXATIN®), and BBR3464. Examples of other agents that can be included within an albumin-containing nanoparticle/antibody complex provided herein include, without limitation, adriamycin, cyclophosphamide, vincristine, prednisone, dexamethasone, cytarabine, methotrexate, thiotepa, ifosfamide, chlorambucil, dacarbazine, bleomycin, ibrutinib, campath-B, gemcitabine, revlimid, sirolimus, temsirolimus, bexxar, brentuximab, bendamustine, and etoposide. For example, an albumin-containing nanoparticle/antibody complex provided herein (e.g., ABRAXANE®/anti-CD52 polypeptide antibody complex, e.g., ABRAXANE®/anti-CD20 polypeptide antibody complex, and e.g., ABRAXANE®/anti-CD38 polypeptide antibody complex) can include brentuximab, cyclophosphamide, adriamycin, or vincristine as part of the complex.

Any appropriate method can be used to administer an albumin-containing nanoparticle/antibody complex provided herein (e.g., an ABRAXANE®/anti-CD52 polypeptide antibody complex, an ABRAXANE®/anti-CD20 polypeptide antibody complex, and an ABRAXANE®/anti-CD38 polypeptide antibody complex) to a mammal. For example, a composition containing albumin-containing nanoparticle/antibody complexes such as ABRAXANE®/anti-CD20 polypeptide antibody complexes can be administered via injection (e.g., subcutaneous injection, intramuscular injection, intravenous injection, or intrathecal injection).

Before administering a composition containing an albumin-containing nanoparticle/antibody complex provided herein (e.g., ABRAXANE®/antibody complexes) to a mammal, the mammal can be assessed to determine whether or not the mammal has a hematologic cancer and, if so, what type of cancer it is, e.g., a leukemia, a lymphoma or myeloma. Any appropriate method can be used to determine whether or not a mammal has a hematologic cancer and the type of hematologic cancer. For example, a mammal (e.g., human) can be identified as having hematologic cancer, e.g., leukemia, lymphoma or myeloma, using standard diagnostic techniques. In some cases, a tissue biopsy (e.g., lymph node tissue sample) can be collected and analyzed to determine whether or not a mammal has a hematologic cancer.

After identifying a mammal as having hematologic cancer and the type of hematologic cancer, the mammal can be administered a composition containing albumin-containing nanoparticle/antibody complexes provided herein (e.g., ABRAXANE®/anti-CD52 polypeptide antibody complexes for a leukemia, ABRAXANE®/anti-CD20 polypeptide antibody complexes for a leukemia or lymphoma, or ABRAXANE®/anti-CD38 polypeptide antibody complexes for a myeloma).

A composition containing albumin-containing nanoparticle/antibody complexes provided herein (e.g., ABRAXANE®/anti-CD52 polypeptide antibody complexes, ABRAXANE®/anti-CD20 polypeptide antibody complexes or ABRAXANE®/anti-CD38 polypeptide antibody complexes) can be administered to a mammal in any appropriate amount, at any appropriate frequency, and for any appropriate duration effective to achieve a desired outcome (e.g., to increase progression-free survival). In some cases, a composition containing albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes) can be administered to a mammal having hematologic cancer to reduce the progression rate of the lymphoma by 5, 10, 25, 50, 75, 100, or more percent. For example, the progression rate can be reduced such that no additional cancer progression is detected. Any appropriate method can be used to determine whether or not the progression rate of hematologic cancer is reduced. For example, the progression rate of the hematologic cancer can be readily assessed. In one example, assaying blood samples or imaging tissue at different time points can be conducted to determine the amount of cancer cells present. The amounts of cancer cells determined within a blood sample or tissue at different times can be compared to determine the progression rate. After treatment as described herein, the progression rate can be determined again over another time interval.

In some cases, the stage of cancer (e.g., leukemia, lymphoma, or myeloma) after treatment can be determined and compared to the stage before treatment to determine whether or not the progression rate was reduced.

In some cases, a composition containing albumin-containing nanoparticle/antibody complexes provided herein (e.g., ABRAXANE®/anti-CD52 polypeptide antibody complexes, ABRAXANE®/anti-CD20 polypeptide antibody complexes or ABRAXANE®/anti-CD38 polypeptide antibody complexes) can be administered to a mammal having a hematologic cancer under conditions where progression-free survival is increased (e.g., by 5, 10, 25, 50, 75, 100, or more percent) as compared to the median progression-free survival of corresponding mammals having an untreated hematologic cancer of the same type or the median progression-free survival of corresponding mammals having a hematologic cancer treated with ABRAXANE® and an antibody (e.g., an anti-CD52 polypeptide antibody, an anti-CD20 polypeptide antibody, or an anti-CD38 polypeptide antibody) without forming ABRAXANE®/antibody complexes (e.g., without forming ABRAXANE®/anti-CD20 polypeptide antibody complexes). In some cases, a composition containing albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes) can be administered to a mammal having a hematologic cancer to increase progression-free survival by 5, 10, 25, 50, 75, 100, or more percent as compared to the median progression-free survival of corresponding mammals having the hematologic cancer and having received ABRAXANE® or an antibody (e.g., an anti-CD52 polypeptide antibody, anti-CD20 polypeptide antibody, or anti-CD38 polypeptide antibody) alone. Progression-free survival can be measured over any length of time (e.g., one month, two months, three months, four months, five months, six months, or longer).

In some cases, a composition containing albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes) can be administered to a mammal having a hematologic cancer under conditions where the 8-week progression-free survival rate for a population of mammals is 65% or greater (e.g., 66%, 67%, 68%, 69%, 70%, 71%, 72%, 73%, 74%, 75%, 76%, 77%, 78%, 79%, 80% or greater) than that observed in a population of comparable mammals not receiving a composition containing albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes). In some cases, a composition containing albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes) can be administered to a mammal having a hematologic cancer under conditions where the median time to progression for a population of mammals is at least 150 days (e.g., at least 155, 160, 163, 165, or 170 days).

The results presented herein see, e.g., FIG. 1, demonstrate that the dose of the albumin-containing nanoparticle/antibody complexes is critical in achieving inhibition and regression of tumor growth. An effective amount of a composition containing albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes) can be any amount that reduces the progression rate of the hematologic cancer, increases the progression-free survival rate, or increases the median time to progression without producing significant toxicity to the mammal. An effective dosage amount of ABRAXANE® is from about 75 mg/m$^2$ to about 250 mg/m$^2$, 100 mg/m$^2$ to about 200 mg/m$^2$, or about 150 mg/m$^2$. An effective dosage amount of an anti-CD52 polypeptide antibody, e.g., Alemtuzumab, anti-CD20 polypeptide antibody such as Rituximab, and anti CD38 polypeptide antibody, e.g., SAR650984 can be from about 17.5 mg/m$^2$ to about 125 mg/m$^2$, about 35 mg/m$^2$ to about 100 mg/m$^2$, and about 50 to about 100 mg/m$^2$.

If a particular mammal fails to respond to a particular amount, then the amount of ABRAXANE® or anti-CD52, anti-CD20, or anti-CD38 polypeptide antibody can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the hematologic cancer may require an increase or decrease in the actual effective amount administered.

The frequency of administration can be any frequency that reduces the progression rate of the hematologic cancer, increases the progression-free survival rate, or increases the median time to progression without producing significant toxicity to the mammal. For example, the frequency of administration can be from about once every three months, once a month to about three times a month, or from about twice a month to about six times a month, or from about once every two months to about three times every two months. The frequency of administration can remain constant or can be variable during the duration of treatment. A course of treatment with a composition containing ABRAXANE®/antibody complexes can include rest periods. For example, a composition containing ABRAXANE®/antibody complexes can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the hematologic cancer may require an increase or decrease in administration frequency.

An effective duration for administering a composition provided herein can be any duration that reduces the progression rate of the hematologic cancer, increases the progression-free survival rate, or increases the median time to progression without producing significant toxicity to the mammal. Thus, the effective duration can vary from several days to several weeks, months, or years. In general, the effective duration for the treatment of the hematologic cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the hematologic cancer.

A composition containing albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes) can be in any appropriate form. For example, a composition provided herein can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, mannitol, or combinations thereof.

After administering a composition provided herein to a mammal, the mammal can be monitored to determine whether or not the hematologic cancer was treated. For example, a mammal can be assessed after treatment to determine whether or not the progression rate of the cancer was reduced (e.g., stopped). As described herein, any method can be used to assess progression and survival rates.

In some cases, a formulation of ABRAXANE®/Rituxan complexes described in Example 1 can be administered to a human patient having a leukemia or a lymphoma to effect cancer cell death as described in the methods set forth in Example 2.

In some cases, nanoparticles containing albumin (e.g., nanoparticles with an albumin shell) and an agent other than paclitaxel can be used as described herein in place of or in combination with ABRAXANE®. For example, albumin-containing nanoparticles designed to carry a cancer chemotherapeutic agent can be used to form nanoparticle/anti-CD20 polypeptide antibody (or anti-CD52 polypeptide antibody or anti-CD38 polypeptide antibody) complexes that can be used as described herein. An example of such a cancer chemotherapeutic agent includes, without limitation, vinblastine and cyclophosphamide.

In some cases, a composition can be formulated to include nanoparticles containing albumin (e.g., nanoparticles with an albumin shell) that are conjugated to an antibody, agent, or combination of antibodies and agents to form complexes for treating a hematologic cancer. For example, albumin nanoparticles can be formulated to include adriamycin, cyclophosphamide, vincristine, prednisone, dexamethasone, cytarabine, methotrexate, thiotepa, ifosfamide, chlorambucil, dacarbazine, bleomycin, ibrutinib, campath-B, gemcitabine, revlimid, sirolimus, temsirolimus, bexxar, brentuximab, bendamustine, etoposide, or combinations thereof with or without including rituximab.

In some cases, nanoparticles containing albumin (e.g., nanoparticles with an albumin shell) or a complex described herein (e.g., ABRAXANE®/Alemtuzumab complexes, ABRAXANE®/SAR650984 complexes, or ABRAXANE®/rituximab complexes) can be formulated to include one or more anti-chronic inflammation treatment agents designed to reduce the global state of immune dysfunction and/or chronic inflammation present within a cancer patient. For example, steroidal anti-inflammatory agents (e.g., prednisone), non-steroidal anti-inflammatory agents (e.g., naproxen), lympho-depleting cytotoxic agents (e.g., cyclophosphamide), immune cell and/or cytokine targeting antibodies (e.g., infliximab), or a combination thereof can be incorporated into nanoparticles containing albumin or ABRAXANE®/Alemtuzumab complexes, ABRAXANE®/SAR650984 complexes, or ABRAXANE®/Rituximab complexes. In some cases, anti-IL-4 agents (e.g., anti-IL-4 antibodies), anti-IL-13 agents (e.g., soluble IL-13 receptor), and combinations thereof can be incorporated into nanoparticles containing albumin or ABRAXANE® I rituximab complexes.

Any appropriate method can be used to assess whether or not the global state of immune dysfunction and/or chronic inflammation was reduced following an anti-chronic inflammation treatment. For example, cytokine profiles (e.g., IL-4, IL-13, IL-4, IL-13, IL-5, IL-10, IL-2, and interferon gamma) present in blood can be assessed before and after an anti-chronic inflammation treatment to determine whether or not the global state of immune dysfunction and/or chronic inflammation was reduced.

Also contemplated herein are unit doses of the pharmaceutical compositions comprising albumin-containing nanoparticle/antibody complexes provided herein (e.g., ABRAXANE®/anti-CD52 polypeptide antibody complexes, ABRAXANE®/anti-CD20 polypeptide antibody complexes, or ABRAXANE®/anti-CD38 polypeptide antibody complexes). A suitable unit dose of the pharmaceutical composition may comprise about 75 mg/m$^2$ to about 250 mg/m$^2$, about 100 mg/m$^2$ to about 200 mg/m$^2$, and about 150 mg/m$^2$ paclitaxel, and from about 17.5 mg/m$^2$ to about 125 mg/m$^2$, about 35 mg/m$^2$ to about 100 mg/m$^2$, and about 50 to about 100 mg/m$^2$ of an antibody described herein.

The invention will be further described in the following examples, which do not limit the scope of the invention described in the claims.

EXAMPLES

Example 1

Preparation of AR160 for mouse injections:

ABRAXANE® was reconstituted with Rituxan in 0.5 ml of 0.9% saline to provide a final concentration of 10 mg/ml paclitaxel and 4 mg/ml Rituxan. The solution was then incubated at room temperature for 30 minutes to allow the formation complexes of albumin-paclitaxel and Rituxan, AR160. The AR160 solution was then diluted in 0.9% saline as follows for administration to mice: For AR160 30, 60u1 of the AR160 solution was added to 40 ul 0.9% saline; For AR160 45, 90 ul of AR160 solution was added to 10 ul 0.9% saline. 100 ul of AR160 30 or AR 160 45 were injected intravenously into lymphoma (Daudi cell line) tumor bearing athymic nude mice by the tail vein injection. The final concentration of each drug given to the mice were 30 mg/kg paclitaxel and 12 mg/kg Rituxan for AR160 30 and 45 mg/kg paclitaxel and 18 mg/kg Rituxan for AR160 45.

Controls for this experiment were 100 ul of 0.9% saline (PBS), 100 ul of ABRAXANE® resuspended in 0.9% saline to provide a dose of 30 mg/kg paclitaxel (ABX30), 100 ul of ABRAXANE® resuspended in 0.9% saline to provide a dose of 45 mg/kg paclitaxel (ABX45), 100 ul of Rituxan resuspended in 0.9% saline to provide a dose of 12 mg/kg (RIT12), and 100 ul of Rituxan resuspended in 0.9% saline to provide a dose of 18 mg/kg (RIT18), injected intravenously into lymphoma (Daudi cell line) tumor bearing athymic nude mice by tail vein injection.

The percent change in the tumor size from baseline and survival of were then monitored. The results are presented in FIG. 1 and FIG. 2.

FIG. 1 presents a graph plotting percent change at ten days in tumor size from baseline of the lymphoma bearing nude mice treated with PBS, RIT12, RIT18, ABX30, ABX45, AR160 30 and AR160 45.

Figure 2:
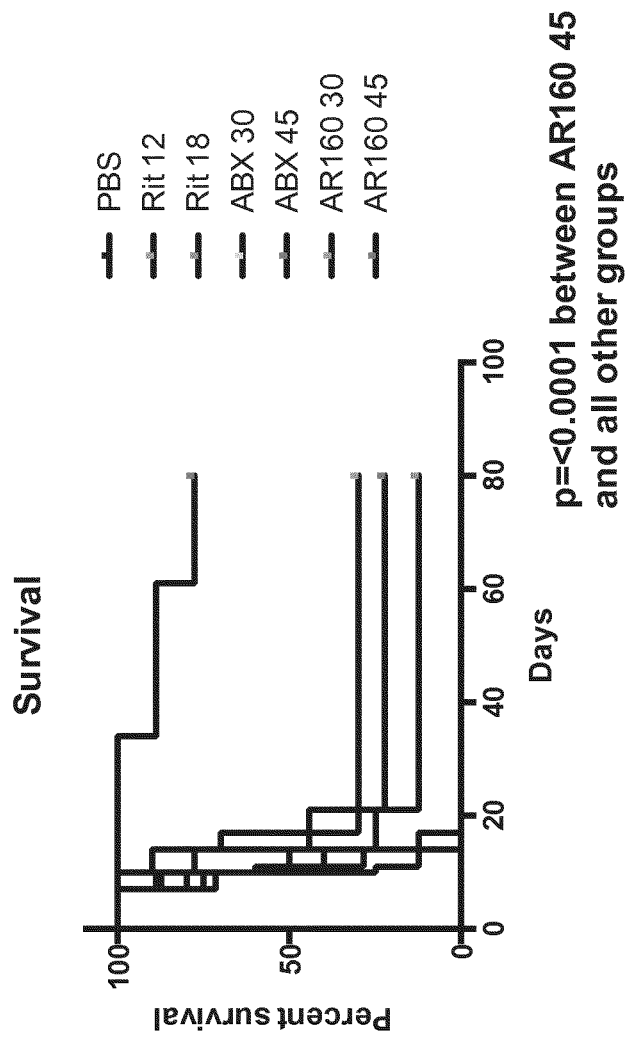
FIG. 2 is a Kaplan Meier graph plotting survival of lymphoma (Daudi cell line) tumor bearing nude mice treated with PBS, Rituxan (RIT12; 12 mg/kg) only, Rituxan (RIT18; 18 mg/kg) only ABX30 (ABRAXANE®, 30 mg/kg) only, ABX 45 (ABRAXANE®, 45 mg/kg) only, or AR160 complexes, AR160 30 (ABX 30 mg/kg, RIT 12 mg/kg), AR160 45 (ABX 45 mg/kg, RIT 18 mg/kg). At 80 days 9/9 AR160 45 mice responded to therapy and 2 progressed, ⅞ complete responses. The graph illustrated the criticality of the effective dose of AR160 wherein the survival rate more than triples as compared to the effect of Rituxan or ABRAXANE® alone.

FIG. 2 is a Kaplan Meier graph plotting survival of the mice treated with PBS, Rituxan (RIT12; 12 mg/kg) only, Rituxan (RIT18; 18 mg/kg) only ABX30 (30 mg/kg paclitaxel) only, ABX 45 (45 mg/kg paclitaxel) only, or AR160 complexes, AR160 30 (paclitaxel 30 mg/kg, RIT 12 mg/kg), AR160 45 (paclitaxel 45 mg/kg, RIT 18 mg/kg). At 80 days from administration 9/9 AR160 45 mice responded to therapy: 2 progressed and 7/9 had complete responses in that the tumor was undetectable by visual inspection. The graph illustrates the criticality of the effective dose of AR160 wherein the survival rate more than triples as compared to the effect of Rituxan or ABRAXANE® alone.

Example 2

ABRAXANE®/Rituxan complexes as Targeted Therapy for Lymphomas

A treatment schedule for ABRAXANE®/Rituxan complexes is repeated each month (every 28 days +/−3 days) or until disease progression, patient refusal, or unacceptable toxicity (Table 1) with the indicated dose escalation scheme (Table 2) and dose limiting toxicities (Table 3).

TABLE 1

| Agent | Dose | Route | Days | ReRx |
|---|---|---|---|---|
| ABRAXANE ®/ Rituxan complexes | assigned at time of registration | IV over 60 minutes (only 1$^{st}$ dose; subsequent doses infused over 30 minutes) | 1, 8 and 15 | Every 28 days* |

*One treatment cycle = 28 days +/− 3 days

TABLE 2

Dose Escalation Scheme.

| Dose Level | Dose (ABX) | Dose (RIT) |
|---|---|---|
| −2 | 75 mg/m$^2$ | 30 mg/m$^2$ |
| −1 | 100 mg/m$^2$ | 40 mg/m$^2$ |
| 1* | 125 mg/m$^2$ | 50 mg/m$^2$ |
| 2 | 150 mg/m$^2$ | 60 mg/m$^2$ |
| 3 | 175 mg/m$^2$ | 70 mg/m$^2$ |

*Starting dose.

TABLE 3

Dose Limiting Toxicities (DLT).

| Toxicity | DLT Definition |
|---|---|
| Hematologic | Grade 4 ANC, Grade 4 Hgb, or PLT <25,000 |
| Renal | Serum creatinine ≥2 times baseline |
| Other nonhematologic | ≥grade 3 as per NCI Common Terminology Criteria for Adverse Events (CTCAE) version 4.0 |

ABRAXANE®/Rituxan Complexes

ABRAXANE®/Rittman complexes are prepared as a hazardous low risk product. ABRAXANE® is supplied as a white to off-white lyophilized powder containing 100 mg of paclitaxel and approximately 900 mg Albumin Human USP (HA) as a stabilizer in a 50 mL, single-use vial. Each vial of the lyophilized product is reconstituted as set forth below. Unreconstituted ABRAXANE® is stored at controlled room temperature in its carton. Reconstituted ABRAXANE® is used immediately. Rituxan is classified as an anti-CD20 monoclonal antibody.

The dose appropriate number of vials of Rituxan are obtained, and each vial is further diluted per the following directions to 4 mg/mL. The dose appropriate number of ABRAXANE® (paclitaxel) 100 mg vials is obtained and each vial is reconstituted per the following directions to a final concentration containing 10 mg/mL nanoparticle albumin-bound (nab) paclitaxel. It is not a requirement to use filter needles in the preparation of, or in-line filters during administration. In addition, filters of pore-size less than 15 micrometers are to be avoided.

As with other cytotoxic anticancer drugs, caution is exercised in handling ABRAXANE®. The use of gloves is recommended.

Using a sterile 3 mL syringe, 1.6 mL (40 mg) of Rituxan 25 mg/mL is withdraw and slowly injected, over a minimum of 1 minute, onto the inside wall of each of the vials containing 100 mg of ABRAXANE®. Unused Rituxan left in the 25 mg/mL vial is discarded, as the product contains no preservatives. Injecting the Rituxan solution directly onto the lyophilized cake is avoided as this will result in foaming. Using a sterile 12 mL sterile syringe, 8.4 mL of 0.9% Sodium Chloride Injection, USP, is withdrawn and slowly injected, over a minimum of 1 minute, onto the inside wall of each vial containing ABRAXANE® 100 mg and Rituxan 40 mg. Once the addition of Rituxan 1.6 mL and 0.9% Sodium Chloride Injection, USP 8.4 mL is complete in each vial, each vial is gently swirled and/or inverted slowly for at least 2 minutes until complete dissolution of any cake/powder occurs. The generation of foam is avoided. The concentration of each vial is 100 mg/10 mL ABRAXANE® and 40 mg/10 mL Rituxan. The vials containing the ABRAXANE® and Rituxan are allowed to sit for 60 minutes. The vial(s) are gently swirled and/or inverted every 10 minutes to continue to mix the complexes. After 60 minutes is elapsed, a sterile 60- to 100-mL syringe (appropriate size for the volume being administered) is used to withdraw the calculated dosing volume of ABRAXANE® and Rituxan from each vial. A sufficient quantity of 0.9% Sodium Chloride Injection, USP is added to make the final concentration of ABRAXANE® 5 mg/mL and Rittman 2 mg/mL. The syringe is gently swirled and/or inverted slowly for 1 minute to mix. The storage and stability is for up to 4 hours at room temperature following final dilution.

Determination of Maximum Tolerated Dose (MTD)

The maximum tolerated dose is defined as the highest dose level among those tested where at most one out of six patients develops a DLT prior to the start of their second cycle of treatment and the next highest dose level is such that two out of a maximum of six patients treated at this dose level developed a DLT prior to the start of their second cycle of treatment.

Enrollment and Determination of MTD

A minimum of two or a maximum of six patients are accrued to a given dose level. For dose level 1 (and if accrued to, dose levels −1 & −2), enrollment is temporarily halted after each patient has been enrolled in order to gather acute adverse event data over the first cycle of their treatment. For dose levels 2 & 3, patients are accrued to these dose levels so that at any given time no more than two patients are receiving their first cycle of treatment and acute adverse event data over the first treatment cycle for all other patients treated at the current dose level is known. If, at any time in the enrollment process, two patients treated at the current dose level develop a DLT during the first cycle of treatment, enrollment is closed to that dose level. Enrollment is re-opened to the next lower dose level if fewer than six patients have been treated at that dose level. If none of the first three patients treated at a given dose level develops a DLT during the first cycle of treatment, enrollment to the dose level is closed and enrollment is reopen at next higher dose level. If there are no other higher dose levels to be tested, three additional patients are enrolled at the current dose level to confirm MTD. If one of the first three patients treated at a given dose level develops a DLT during the first cycle of treatment, three additional patients are enrolled (sequentially) onto the current dose level. If, at any time in the enrollment of these three additional patients, a patient develops a DLT, enrollment is closed to this dose level. Enrollment is re-opened to the next lower dose level if fewer than six patients are treated at that dose level. If none of these three additional patients develops a DLT during the first cycle of treatment, enrollment to this dose level is closed and enrollment is reopened at next higher dose level. If there are no other higher dose levels to be tested, this is considered the MTD.

For this protocol, the patient returns for evaluation and retreatment (at least every 28 +/−3 days) according to the schedule. If a patient fails to complete the first cycle of treatment for reasons other than toxicity, an additional patient is enrolled to replace this patient.

Dosage Modification Based on Adverse Events

The modifications in Table 4 are followed until individual treatment tolerance is ascertained. If multiple adverse events (Table 5) are seen, dose is administered based on greatest reduction required for any single adverse event observed. Dose modifications apply to the treatment given in the preceding cycle and are based on adverse events observed since the prior dose.

TABLE 4

Dose Levels Based on Adverse Events.
ABRAXANE ®/Rituxan complexes-
Both drugs are reduced

| Dose Level | ABX dose | Accompanying RIT dose (40% of ABX dose) |
|---|---|---|
| 2 | 175 mg/m$^2$ | 70 mg/m$^2$ |
| −1 | 150 mg/m$^2$ | 60 mg/m$^2$ |
| 1 | 125 mg/m$^2$ | 50 mg/m$^2$ |
| −2 | 100 mg/m$^2$ | 40 mg/m$^2$ |
| −2 | 75 mg/m$^2$ | 30 mg/m$^2$ |

*Dose level 1 refers to the starting dose.

TABLE 5

Use Common Terminology Criteria for Adverse Events (CTCAE) v. 4.0*
unless otherwise specified

| CTCAE Category | Adverse Event | Dose Reduction |
|---|---|---|
| Investigations | ANC <1000 or PLT <75,000 | Day 1: Hold until counts above these levels. Day 8: Omit dose that day and retreat at same dose level on day 15 if counts have recovered. Day 15: Omit dose that day. NOTE: if two consecutive cycles of therapy require omission of a dose, subsequent treatment cycles should begin (day 1) at next lower dose. |
| | AST or Alkaline Phosphatase ≥Grade 2 | Day 1: Hold until resolved to <Grade 2 then reduce dose by ONE dose level. If treatment needs to be held >4 weeks, discontinue study treatment and go to event monitoring. |

TABLE 5-continued

Use Common Terminology Criteria for Adverse Events (CTCAE) v. 4.0*
unless otherwise specified

| CTCAE Category | Adverse Event | Dose Reduction |
|---|---|---|
| Neurology disorders | Neuropathy ≥Grade 2 | Day 1: Hold until resolved to <Grade 2 then reduce dose by ONE dose level.<br>Day 8 OR 15- Omit dose that day. If resolved to <Grade 2 by next scheduled dose, then dose reduce by one level<br>If treatment needs to be held >4 weeks, discontinue study treatment and go to Event Monitoring |
| All other non-hematologic adverse events | ≥Grade 3 | Day 1: Hold until resolved to < Grade 2 then reduce dose by ONE dose level.<br>Day 8: Omit dose that day. If resolved to ≤Grade 2 by day 15, then dose reduce by one level and retreat.<br>Day 15: Omit dose that day.<br>NOTE: if two consecutive cycles of therapy require omission of a dose, subsequent treatment cycles should begin (day 1) at next lower dose.<br>If treatment needs to be held >4 weeks, discontinue study treatment and go to Event Monitoring |
| Gastrointestinal Disorders | Bowel perforation Bowel Obstruction | Discontinue all study treatment and proceed to Event Monitoring |
| | Grade 1 | Continue patient on study for partial bowel obstruction NOT requiring medical intervention. |
| | Grade 2 | Hold for partial obstruction requiring medical intervention. If resolved to Grade 0 within 4 weeks, treatment may be restarted. If treatment needs to be held >4 weeks, discontinue all study treatment and go to Event Monitoring. |
| | Grade 3 or 4 | For complete bowel obstruction, discontinue study treatment and proceed to Event Monitoring |
| Cardiac Disorders | Hypertension ≥Grade 3 | Hypertension should be treated as per general practice. If hypertension (≥150/100) persists despite treatment, hold treatment until blood pressure is below this level<br>If treatment needs to be held >4 weeks due to uncontrolled hypertension, discontinue study treatment and go to Event Monitoring. |
| | Left ventricular systolic | |
| | function- Grade 3 | Hold until resolution to Grade ≤1. If treatment needs to be held >4 weeks, discontinue all study treatment and go to Event Monitoring. |
| | Grade 4 | Discontinue treatment and proceed to Event Monitoring |
| Respiratory, thoracic and | Bronchopulmonary Hemorrhage | |
| mediastinal disorders | ≥Grade 2 | Discontinue all study treatment and proceed to Event Monitoring |
| Coagulation | Hemorrhage | |
| | Grade 3 | Hold until ALL of the following criteria are met:<br>1. Bleeding has resolved and Hb is stable.<br>2. There is no bleeding diathesis that would increase the risk of therapy.<br>3. There is no anatomic or pathologic condition that could increase the risk of hemorrhage recurrence. |
| | Grade 4 | If treatment needs to be held >4 weeks, discontinue study treatment and go to Event Monitoring<br>Patients who experience a recurrence of Grade 3 hemorrhage are to discontinue all study treatment and proceed to Event Monitoring.<br>Discontinue study treatment and proceed to Event Monitoring |

TABLE 5-continued

Use Common Terminology Criteria for Adverse Events (CTCAE) v. 4.0*
unless otherwise specified

| CTCAE Category | Adverse Event | Dose Reduction |
|---|---|---|
| Vascular disorders | Bleeding diathesis Grade 3 or 4 Venous thrombosis | Discontinue study treatment and proceed to Event Monitoring |
| | Grade 3 or asymptomatic Grade 4 | Hold treatment. If the planned duration of full-dose anticoagulation is <2 weeks, treatment should be held until the full-dose anticoagulation period is over. If the planned duration of full-dose anticoagulation is >2 weeks, treatment may be resumed during the period of full-dose anticoagulation IF all of the criteria below are met: The subject must have an in-range INR (usually 2-3) on a stable dose of warfarin, or on stable dose of heparin prior to restarting treatment. |
| | Symptomatic Grade 4 | The subject must not have pathological conditions that carry high risk of bleeding (e.g. tumor involving major vessels or other conditions) The subject must not have had hemorrhagic events while on study If thromboemboli worsen/recur upon resumption of study therapy, discontinue treatment. Discontinue treatment and proceed to Event Monitoring |
| | Arterial thrombosis (Angina, myocardial infarction, transient ischemic attack, cerebrovascular accident, or any other arterial thromboembolic events) ANY Grade | Discontinue treatment and proceed to Event Monitoring |

Ancillary Treatment/Supportive Care

Routine use of colony-stimulating factors (G-CSF or GM-CSF) is not recommended. Prophylactic use of colony-stimulating factors during the study is not allowed. Therapeutic use in patients with serious neutropenic complications such as tissue infection, sepsis syndrome, fungal infection, etc., may be considered at physician discretion. Recombinant erythropoietin to maintain adequate hemoglobin levels and avoid packed red blood cell transfusions is allowed.

Patients should receive full supportive care while on this study. This includes blood product support, antibiotic treatment and treatment of other newly diagnosed or concurrent medical conditions. All blood products and concomitant medications such as antidiarrheals, analgesics, and antiemetics received from the first administration of study drugs until 30 days after the final dose are to be recorded in the medical record. Patients participating in phase I program clinical trials are not to be considered for enrollment in any other study involving a pharmacologic agent-(drugs, biologics, immunotherapy approaches, gene therapy) whether for symptom control or therapeutic intent.

Hypersensitivity Reactions

Patients do not require premedication prior to administration of ABRAXANE®/Rituxan complexes. In the unlikely event of a hypersensitivity reaction, treatment with antihistamines, H2 blockers, and corticosteroids is recommended. Patients should be pre-medicated with the typical regimen for paclitaxel regimens for subsequent cycles. In the unlikely event of a mild hypersensitivity reaction, premedication may be administered using the premedication regimen the institution typically uses for solvent-based paclitaxel.

Administration

The IV initial complex dose is infused over 60 minutes via syringe pump. The infusion may be shortened to 30 minutes if the initial infusion is well tolerated. Infusion is monitored closely during the infusion process for signs/symptoms of an infusion reaction. The patient's line is flushed after administration with 20 mL 0.9% Sodium Chloride. An example calculation and preparation is as follows:

Dose level 1: ABRAXANE® 125 mg/m$^2$/Rituxan 50 mg/m$^2$ BSA=2 m$^2$

Doses required: ABRAXANE® 250 mg/Rituxan 100 mg

Obtain three 100 mg vials of ABRAXANE®.

Obtain one 100 mg vial of Rituxan 25 mg/mL.

Withdraw 1.6 mL (40 mg) of Rituxan 25 mg/mL and slowly inject over 1 minute onto the inside wall of one of the 100 mg ABRAXANE® vials. Repeat this procedure for each of the remaining two ABRAXANE® 100 mg vials.

Add 8.4 mL 0.9% Sodium Chloride Injection, USP onto the inside wall of one of the vials containing ABRAXANE® and Rituxan. Repeat this procedure for each of the remaining two ABRAXANE® and Rituxan vials.

Let mixture sit for 60 minutes (swirling every 10 minutes). The final concentration of each vial should be 100 mg ABRAXANE®/10 mL and 40 mg Rituxan/10 mL.

Withdraw 25 mL from the ABRAXANE® and Rituxan containing vial and place in a 100 mL sterile syringe. Add 25 mL 0.9% Sodium Chloride Injection, USP for a final ABRAXANE® concentration of 5 mg/mL and Rituxan concentration of 2 mg/mL. Infuse via syringe pump over 60 minutes (first dose, 30 minutes subsequent doses).

Response to ABRAXANE®/Rituxan Complex Treatment

Each patient's response to treatment with a ABRAXANE®/Rituxan complex formulation is monitored.

What is claimed is:

1. A unit dose of a composition comprising albumin-containing nanoparticles complexed with an antibody wherein said nanoparticles contain albumin and paclitaxel at a ratio of about 9:1 albumin to paclitaxel as well as a plurality of humanized antibodies complexed thereto wherein said nanoparticles are solids which have a size less than 1 micron provided that at least a portion of the said antibodies are arranged in a manner that said nanoparticle complexes retain antibody mediated target binding specificity and wherein the antibody is an anti-CD52 polypeptide humanized antibody, wherein said unit dose comprises from about 17.5 mg/m$^2$ to about 125 mg/m$^2$ of said antibody and about 75 mg/m$^2$ to about 250 mg/m$^2$ paclitaxel.

2. The unit dose of a composition of claim 1 wherein the antibody is alemtuzumab.

3. The unit dose of a composition of claim 1 wherein the antibodies are non-covalently complexed with the nanoparticles.

4. A method to effect hematological cancer cell death said method comprising contacting the cancer cell with a composition comprising albumin-containing nanoparticles complexed with an antibody wherein said nanoparticles contain albumin and paclitaxel at a ratio of about 9:1 albumin to paclitaxel as well as a plurality of humanized antibodies complexed thereto wherein said nanoparticles are solids which have a size less than 1 micron provided that at least a portion of the said antibodies are arranged in a manner that said nanoparticle-complexes retain antibody mediated target binding specificity and wherein the antibody is an anti-CD52 polypeptide humanized antibody, wherein said unit dose comprises from about 17.5 mg/m$^2$ to about 125 mg/m$^2$ of said antibody and about 75 mg/m$^2$ to about 250 mg/m$^2$ paclitaxel.

5. The method of claim 4, wherein the hematologic cancer cell is a leukemia cell, a lymphoma cell, or myeloma cell.

6. The method of claim 5, wherein the leukemia cell is an acute myelogenous (granulocytic) leukemia (AML) cell, chronic myelogenous (granulocytic) leukemia (CML) cell, acute lymphocytic (lymphoblastic) leukemia (ALL) cell, chronic lymphocytic leukemia (CLL) cell, or hairy cell leukemia).

7. The method of claim 5, wherein the lymphoma cell is a cell of a mature B-cell neoplasm, a mature T cell neoplasm, a mature natural killer cell neoplasm, an immunodeficiency-associated lymphoproliferative disorder, Hodgkin lymphoma cell, and non-Hodgkin lymphoma cell.

8. The method of claim 5, wherein the myeloma is a multiple myeloma cell.

9. The method of claim 4, wherein the unit dose comprises about 100 mg/m$^2$ to about 200 mg/m$^2$ paclitaxel.

10. The method of claim 4, wherein the unit dose comprises about 150 mg/m$^2$ paclitaxel.

11. The method of claim 4, wherein the unit dose comprises about 35 mg/m$^2$ to about 100 mg/m$^2$ of the antibody.

12. The method of claim 4, wherein the unit dose comprises about 50 mg/m$^2$ to about 100 mg/m$^2$ of the antibody.

13. A method for lysing a hematological cancer cell in a patient, the method comprises administering to the patient an effective amount of a composition comprising albumin-containing nanoparticles complexed with an antibody wherein said nanoparticles contain albumin and paclitaxel at a ratio of about 9:1 albumin to paclitaxel as well as a plurality of humanized antibodies complexed thereto wherein said nanoparticles are solids which have a size less than 1 micron provided that at least a portion of the said antibodies are arranged in a manner that said nanoparticle-complexes retain antibody mediated target binding specificity and wherein the antibody is an anti-CD52 polypeptide humanized antibody, wherein said unit dose comprises from about 17.5 mg/m$^2$ to about 125 mg/m$^2$ of said antibody and about 75 mg/m$^2$ to about 250 mg/m$^2$ paclitaxel.

14. The method of claim 13, wherein the unit dose comprise about of 100 mg/m$^2$ to about 200 mg/m$^2$ paclitaxel.

15. The method of claim 13, wherein the unit dose comprise about 150 mg/m$^2$ paclitaxel.

16. The method of claim 13, wherein the unit dose comprise about 35 mg/m$^2$ to about 100 mg/m$^2$ antibody.

17. The method of claim 13, wherein the unit dose comprise about 50 mg/m$^2$ to about 100 mg/m$^2$.

18. The method of claim 13, wherein the hematologic cancer cell is a leukemia cell, a lymphoma cell, or myeloma cell.

19. The method of claim 18, wherein the leukemia cell is an acute myelogenous (granulocytic) leukemia (AML) cell, chronic myelogenous (granulocytic) leukemia (CML) cell, acute lymphocytic (lymphoblastic) leukemia (ALL) cell, chronic lymphocytic leukemia (CLL) cell, or hairy cell leukemia).

20. The method of claim 18, wherein the lymphoma cell is a cell of a mature B-cell neoplasm, a mature T cell neoplasm, a mature natural killer cell neoplasm, an immunodeficiency-associated lymphoproliferative disorder, Hodgkin lymphoma, and non-Hodgkin lymphoma.

21. The method of claim 17, wherein the myeloma is a multiple myeloma cell.

22. The method of claim 13, wherein the patient is a mammal.

23. The method of claim 22, wherein the mammal is a human.

24. The method of claim 13, wherein said pharmaceutical composition comprises a humanized anti-CD52 polypeptide antibody.

* * * * *